(12) United States Patent
Boniface et al.

(10) Patent No.: US 10,294,321 B2
(45) Date of Patent: May 21, 2019

(54) SWITCHABLE MATERIALS, METHODS AND USES THEREOF

(71) Applicant: Kyle J. Boniface, Bowmanville (CA)

(72) Inventors: Kyle J. Boniface, Bowmanville (CA); Timothy James Clark, Kingston (CA); Michael F. Cunningham, Kingston (CA); Philip G. Jessop, Kingston (CA); Brian Ernest Mariampillai, Kingston (CA); Sean M. Mercer, Sarnia (CA); Rui Resendes, Toronto (CA); Tobias Robert, Braunschweig (DE)

(73) Assignee: Kyle J. Boniface, Bowmanville (CA)

( * ) Notice: Subject to any disclaimer, the term of this patent is extended or adjusted under 35 U.S.C. 154(b) by 445 days.

(21) Appl. No.: 15/023,346

(22) PCT Filed: Sep. 18, 2014

(86) PCT No.: PCT/CA2014/050897
§ 371 (c)(1),
(2) Date: Mar. 18, 2016

(87) PCT Pub. No.: WO2015/039247
PCT Pub. Date: Mar. 26, 2015

(65) Prior Publication Data
US 2016/0244548 A1    Aug. 25, 2016

Related U.S. Application Data

(60) Provisional application No. 61/879,486, filed on Sep. 18, 2013.

(51) Int. Cl.
*C09F 9/00*    (2006.01)
*B01D 15/10*    (2006.01)
(Continued)

(52) U.S. Cl.
CPC ............ *C08F 292/00* (2013.01); *B01D 15/10* (2013.01); *B01D 15/40* (2013.01); *B01D 15/426* (2013.01);
(Continued)

(58) Field of Classification Search
CPC ........ C08F 292/00; C08L 101/12; C09F 9/00; G01N 30/032; G01N 2030/027;
(Continued)

(56) References Cited

U.S. PATENT DOCUMENTS

2008/0187758 A1*  8/2008  Yokokawa ............. B05D 1/185
428/411.1

OTHER PUBLICATIONS

S. Kumar, X. Tong, Y.L. Dory, M. Lepage, Y. Zhao, "A CO2-switchable polymer brush for reversible capture and release of proteins", Chem. Commun. 2013, 49, 90-92 (Year: 2012).*
(Continued)

*Primary Examiner* — James C Goloboy
(74) *Attorney, Agent, or Firm* — ABM Intellectual Property Inc.; Adrienne Bieber McNeil

(57) ABSTRACT

The present application provides a composite material that comprises a solid and solid-supported non-polymeric switchable moiety, wherein the switchable moiety comprises a functional group that is switchable between a first form and a second form, said first form being neutral and hydrophobic, and said second form being ionized and hydrophilic. The composite material converts to, or is maintained in, said second form when the switchable moiety is exposed to $CO_2$ at amounts sufficient to maintain the ionized form. The composite material converts to, or is maintained in, said first form when $CO_2$ is removed or reduced to an amount insufficient to maintain the ionized form. $CO_2$ is removed or reduced by exposing the composite material to heat and/or a flushing inert gas such as $N_2$, Ar, or air. Envisioned uses of these composite materials includes removing water from
(Continued)

non-aqueous solvents, removing water vapor from gaseous mixtures, and cleaning industrial reaction vessels and/or pipelines.

15 Claims, 20 Drawing Sheets

(51) Int. Cl.

| | |
|---|---|
| *B01D 15/40* | (2006.01) |
| *B01D 15/42* | (2006.01) |
| *B01D 53/26* | (2006.01) |
| *B01J 19/02* | (2006.01) |
| *B01J 20/26* | (2006.01) |
| *B01J 20/32* | (2006.01) |
| *G01N 30/02* | (2006.01) |
| *B01J 20/286* | (2006.01) |
| *B01J 20/289* | (2006.01) |
| *C08F 292/00* | (2006.01) |
| *C08L 101/12* | (2006.01) |

(52) U.S. Cl.
CPC ............ *B01D 53/26* (2013.01); *B01D 53/261* (2013.01); *B01J 19/02* (2013.01); *B01J 20/265* (2013.01); *B01J 20/286* (2013.01); *B01J 20/289* (2013.01); *B01J 20/3204* (2013.01); *B01J 20/3219* (2013.01); *B01J 20/3259* (2013.01); *B01J 20/3293* (2013.01); *C08L 101/12* (2013.01); *C09F 9/00* (2013.01); *G01N 30/02* (2013.01); *B01J 2219/00024* (2013.01); *B01J 2219/0245* (2013.01); *B01J 2220/54* (2013.01); *G01N 2030/027* (2013.01)

(58) Field of Classification Search
CPC ...... B01D 15/10; B01D 15/40; B01D 15/426; B01D 53/26; B01D 53/261; B01J 20/265; B01J 20/286; B01J 20/289; B01J 20/3204; B01J 20/3219; B01J 20/3259; B01J 20/3293
See application file for complete search history.

(56) References Cited

OTHER PUBLICATIONS

Electronic Supplementary Information (ESI) for the Kumar article, retrieved from the internet at <http://www.rsc.org/suppdata/cc/c2/c2cc36284h/c2cc36284h.pdf> on Jul. 30, 2018. (Year: 2012).*

International Search Report issued in corresponding application No. PCT/CA2014/050897 dated Nov. 25, 2014 (3 pages).

Written Opinion of the International Searching Authority issued in corresponding application No. PCT/CA2014/050897 dated Nov. 25, 2014 (4 pages).

International Preliminary Report on Patentability issued in corresponding application No. PCT/CA2014/050897 dated Dec. 10, 2015 (20 pages).

Kumar, S. et al, "A CO2-switchable polymer brush for reversible capture and release of proteins"; ChemComm 2013, 49, pp. 90-92; Published Nov. 9, 2012 (3 pages).

Anchao, F. et al, "CO2-Stimuli Responsive Polymers"; Progress in Chemistry, vol. 24, No. 10, 1995-2003; Published Oct. 2012 (9 pages).

Paumier, G. et al, "Thermoresponsive polymer-based microdevice for nano-liquid chromatography"; Biodevices 2008—International Conference on Biomedical Electronics and Devices 2008, pp. 178-181 (4 pages).

Mohammed, F.S. et al, "Dynamic Surface Properties of Amino-Terminated Self-Assembled Monolayers Incorporating Reversible CO2 Chemistry"; Industrial & Engineering Chemistry Research 2011, 50, pp. 8034-8041; Published May 30, 2011 (8 pages).

Boniface, K.J. et al, "Switchable Hydrophilicity Surface, Incorporating CO2 as a Reversible Trigger"; 96th Canadian Chemistry Conference and Exhibition 2013; Published May 22, 2013 (1 page).

* cited by examiner

SWITCHABLE MATERIALS, METHODS AND USES THEREOF

CROSS-REFERENCE TO RELATED APPLICATIONS

This application is a national phase application of PCT/CA2014/050897, filed on Sep. 18, 2014. PCT/CA2014/050897 claims priority to U.S. Provisional Application Ser. No. 61/879,486, filed on Sep. 18, 2013. Both PCT/CA2014/050897 and U.S. Provisional Application Ser. No. 61/879,486 are hereby incorporated by reference in their entirety.

FIELD OF THE INVENTION

The present application pertains to the field of materials science. More particularly, the present application relates to materials that are switchable between two distinct forms, and methods of manufacture and uses thereof.

INTRODUCTION

Recently, materials with stimuli-responsive properties have been developed. These materials are sometimes referred to as "smart materials", and they rely on external stimuli, such as temperature, electrical potential, pH, and/or light, to induce property changes. There are a wide variety of applications for which use of smart materials could be desirable. Examples of applications for which smart materials are being developed include, but are not limited to, removal of water from non-aqueous liquids, and cleaning of industrial reaction vessels or pipelines.

Water removal from non-aqueous liquids is an expensive necessity in many industrial processes. The presence of water in fuel reduces heat of fuel combustion and causes corrosion of fuel system components (such as fuel and injector pumps). Biofuels, obtained from cellulosic materials, are often contaminated with water and, thus, require a costly distillation to reach acceptable water content levels. Moreover, some valuable non-aqueous liquids cannot be dried by simple distillation because they form azeotropes with water. In such cases, more expensive azeotrope-breaking methods are required. Three popular methods of drying non-aqueous solvents include: a) the use of distillation with metals or metal hydrides; b) single-use desiccants; and c) molecular sieves, and each have serious economical and environmental problems. Distillation with highly reactive metals or metal hydrides requires costly heating and carries risk of fires and/or explosions. Single-use desiccants result in large amounts of solid waste, typically wet solid waste that is a combination of desiccant, water, and/or solvent; this can produce disposal issues. Reusable molecular sieves require large amounts of energy for regeneration. As such, there remains a need for a smart material capable of reversibly changing its properties. Such a smart material could be switched between being a desiccant a being a non-desiccant. In desiccant form, it would be capable of capturing water, and in non-desiccant form it would be capable of releasing water when triggered by external stimuli.

Industrial reaction vessels and/or pipelines need to be cleaned after a certain amount of time or product output otherwise they become less efficient and/or hinder reactions. Depending on reaction scale, cleaning vessels and/or pipelines can be a lengthy and labour intensive process. Smart materials that could be used to facilitate industrial scale cleaning by changing their properties, such as switching between hydrophobic and hydrophilic states, are materials that use light, pH, or $CO_2$ to induce said change. A smart material that uses light as its stimulus would require a "dark" form that is compatible with any reaction taking place inside a vessel, or a pipeline as the material is transported, given that most industrial processes occur in closed systems. To switch the smart material's properties, a light would have to be installed within the vessel/pipelines, or the vessel or pipeline's top would have to be removed in order to irradiate the vessel/pipeline with an external source. A potential problem with this system is that all molecules can absorb light: dirt, grime or chemical reside coating a vessel/pipeline may absorb light that is intended to irradiate a vessel or pipeline's surface, preventing such a smart material from changing its properties.

A smart material that uses pH as its stimulus would likely generate a large amount of waste: acid or base would have to be constantly added to maintain pH. A problem with such smart materials is that application of their stimuli must be held constant in order to favour a select property.

A material that uses $CO_2$ as its stimulus was previously described [K. Boniface, et al., "Switchable Hydrophilicity: Amino-Terminated Self-Assembled Monolayers Incorporating Reversible $CO_2$ Chemistry." 96$^{th}$ CSC Canadian Chemistry Conference and Exhibition, (2013) Quebec, Quebec]. However, this system is not switchable since it cannot be readily and/or repeatedly switched between two different states (in this case, it could not be switched between its hydrophobic and hydrophilic states). Rather, this system becomes stuck in one state or the other.

Thus there remains a need for a smart material capable of reversibly changing its properties between two physical states, such as, hydrophobic and hydrophilic states, when triggered by external stimuli.

The above information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide switchable materials and methods, and uses thereof. In accordance with an aspect of the present application, there is provided a composite material that is reversibly switchable between a first form and a second form, said composite material comprising a solid and solid-supported switchable moiety attached to said solid via a linker, wherein the switchable moiety comprises a functional group that is switchable between a neutral form associated with said first form of said composite material, and an ionized form associated with said second form of the composite material. In a specific embodiment, the linker is not a polyamine.

In accordance with one embodiment, there is provided a composite material wherein said first form of the composite material is neutral and hydrophobic and the second form of the composite material is ionized and hydrophilic.

In accordance with another embodiment, there is provided a composite material that converts to or is maintained in said second form when the switchable moiety is exposed to $CO_2$ at an amount sufficient to maintain said switchable moiety in its ionized form, and wherein the composite material converts to or is maintained in said first form when $CO_2$ is removed or reduced to an amount insufficient to maintain said switchable moiety in its ionized form.

In accordance with another embodiment, there is provided a composite material wherein the $CO_2$ is removed or reduced by exposing the composite material to heat and/or a flushing inert gas such as, but not limited to, $N_2$, Ar or air.

In accordance with another embodiment, there is provided a composite material which comprises the neutral form of the switchable moiety bound to a surface via a linker X as in the structure of formula 1,

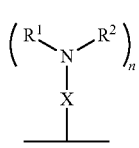 (1)

wherein:
$NR^1R^2$ is a switchable functional group, wherein $R^1$ and $R^2$ are each independently H, a $C_1$ to $C_{10}$ aliphatic group that is linear, branched, or cyclic, a $C_nSi_m$ group where n and m are independently a number from 0 to 10 and n+m is a number from 1 to 10, a $C_5$ to $C_{10}$ aryl group, or a heteroaryl group having 4 to 10 ring atoms, each of which may be substituted; or $R^1$ and $R^2$, together with the atoms to which they are attached, are connected to form a cycle, or heterocycle, each of which may be substituted;

n is an integer 1, 2 or 3; and

X is bonded to the solid and the switchable functional group and is a monovalent or a divalent moiety, such as carbonate, a substituted $C_1$-$C_{15}$ alkyl, $C_1$-$C_{15}$ alkylene, a substituted $C_{15}$-$C_{30}$ alkyl, $C_{15}$-$C_{30}$ alkylene, a substituted $C_1$-$C_{15}$ alkenyl, alkenylene, a substituted $C_{15}$-$C_{30}$ alkenyl, $C_{15}$-$C_{30}$ alkenylene, a substituted $C_1$-$C_{15}$ alkynyl, alkynylene, a substituted $C_{15}$-$C_{30}$ alkynyl, $C_{15}$-$C_{30}$ alkynylene, carbonate alkyl, $C_1$-$C_{15}$ carbonate alkylene, $C_{15}$-$C_{30}$ carbonate alkyl, $C_{15}$-$C_{30}$ carbonate alkylene, $C_1$-$C_{15}$ carbonate alkenyl, $C_1$-$C_{15}$ carbonate alkenlene, $C_{15}$-$C_{30}$ carbonate alkenyl, $C_{15}$-$C_{30}$ carbonate alkenylene, $C_1$-$C_{15}$ carbonate alkynyl, $C_1$-$C_{15}$ carbonate alkynylene, $C_{15}$-$C_{30}$ carbonate alkynyl, $C_{15}$-$C_{30}$ carbonate alkynylene, aryl, arylene, heteroaryl, heteroarylene, thiol, silane, or siloxane, each of which may be substituted; or, X is a monovalent or a divalent cycle, or heterocycle, each of which may be substituted; optionally, X and $R^1$, X and $R^2$ or both, together with the atoms to which they are attached, are connected to form a cycle, or heterocycle, each of which may be substituted; and, wherein the alkylene, alkenylene and alkynylene moieties of X optionally comprise one or more amine, amide, ether, ester, thioether, thioester, silane, siloxane, or a combination thereof, within the hydrocarbon chain, and wherein when X is a monovalent moiety it is bound to the solid via a non-covalent interaction.

In a specific embodiment, the switchable moiety is bound to a surface via a spacer X as in the structure of formula 1a,

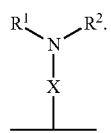 (1a)

In accordance with another embodiment, $R^1$ and $R^2$ of the structure of formula 1 are ethyl.

In accordance with another embodiment, there is provided a composite material which comprises the neutral form of the switchable moiety bound to a surface via a linker X as in the structure of formula 3a, or 3b, or 3c, or any rotational isomers thereof,

 (3a)

 (3b)

 (3c)

wherein:
$N=CR^3NR^4R^5$, $R^3N=CNR^4R^5$, $R^3NH=CR^4NR^5$ are each switchable functional groups, wherein $R^3$, $R^4$, and $R^5$ are independently H, a $C_1$ to $C_{10}$ aliphatic group that is linear, branched, or cyclic; a $C_nSi_m$ group where n and m are independently a number from 0 to 10 and n+m is a number from 1 to 10, a $C_5$ to $C_{10}$ aryl group, or a heteroaryl group having from 4 to 10 carbon atoms in the aromatic ring, each of which may be substituted; or, any combination of $R^3$, $R^4$, and $R^5$, together with the atoms to which they are attached, are connected to form a cycle, or heterocycle, each of which may be substituted;

n is an integer 1, 2 or 3; and

X is bonded to the solid and the switchable functional group and is a monovalent or a divalent moiety, such as a substituted $C_1$-$C_{15}$ alkyl, $C_1$-$C_{15}$ alkylene, a substituted $C_{15}$-$C_{30}$ alkyl, $C_{15}$-$C_{30}$ alkylene, a substituted $C_1$-$C_{15}$ alkenyl, alkenylene, a substituted $C_{15}$-$C_{30}$ alkenyl, $C_{15}$-$C_{30}$ alkenylene, a substituted $C_1$-$C_{15}$ alkynyl, alkynylene, a substituted $C_{15}$-$C_{30}$ alkynyl, $C_{15}$-$C_{30}$ alkynylene, aryl, arylene, heteroaryl, heteroarylene, thiol, silane, or siloxane, each of which may be substituted; or, X is a monovalent or a divalent cycle, or heterocycle, each of which may be substituted; optionally, X and one or two of $R^3$, $R^4$, and $R^5$, together with the atoms to which they are attached, are connected to form a cycle, or heterocycle, each of which may be substituted; and, wherein the alkylene, alkenylene and alkynylene moieties of X optionally comprise one or more amine, amide, ether, ester, thioether, thioester, silane, siloxane, or a combination thereof, within the hydrocarbon chain, and wherein when X is a monovalent moiety it is bound to the solid via a non-covalent interaction.

In a specific embodiment, the material comprises the neutral form of the switchable moiety bound to a surface via a spacer X as in the structure of formula 3'a, or 3'b, or 3'c, or any rotational isomers thereof,

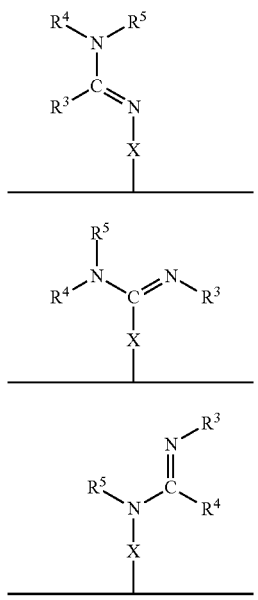

In accordance with another embodiment, $R^3$, $R^4$, and $R^5$ of the structure of formula 3a, or 3b, or 3c, 3'a, or 3b, or 3'c or any rotational isomers thereof, are methyl.

In accordance with another embodiment, there is provided a composite material which comprises the ionized form of the switchable moiety bound to a surface via a spacer X as in the structure of formula 2 or 2a,

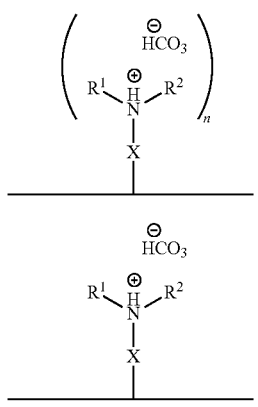

wherein X, n, $R^1$ and $R^2$ are as defined above.

In accordance with another embodiment, there is provided a composite material which comprises the ionized form of the switchable moiety bound to a surface via a spacer X as in the structure of formula 4a, or 4b, or 4c, or 4'a, or 4'b, or 4'c, or any rotational isomers thereof,

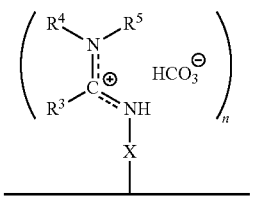

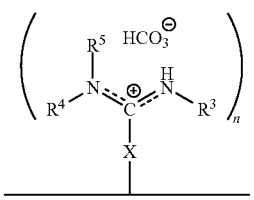

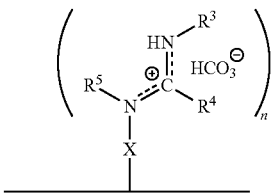

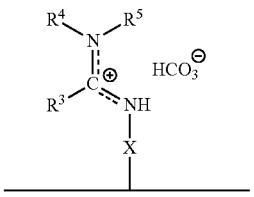

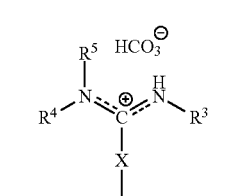

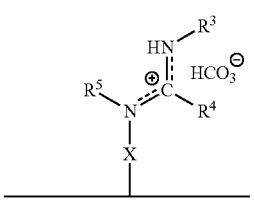

wherein the substituents X, n, $R^3$, $R^4$, and $R^5$ are as defined above.

In accordance with another embodiment, the solid is a polymeric material, such as a polymeric bead or thin film.

In accordance with another embodiment, the polymeric material is a methacrylate polymer or methacrylate copolymer, each of which may be substituted or cross-linked.

In accordance with another embodiment, the solid is a silica, such as, but not limited to, glass, mesoporous silica or silica gel, each of which may be substituted or functionalized.

In accordance with another embodiment, the solid is a semi-metallic or metallic composite material such as, but not limited to steel, silicon wafers, silicon oxides, or gold films, each of which may be alloyed or functionalized.

In accordance with one embodiment, the surface of the solid component of the composite material is rough. This rough surface can impart superhydrophobic properties on the first form of the composite material, and/or superhydrophilic properties on the second form of the composite material.

In accordance with another aspect of the application, there is provided a method for switching between the first form and second form of any one of the composite materials, comprising:

adding a neutral and hydrophobic composite material to an aqueous liquid to form a mixture;

exposing the aqueous mixture to $CO_2$, thereby protonating the switchable moiety and rendering the composite material ionized and hydrophilic;

optionally separating the ionized hydrophilic composite material from the mixture;

exposing the ionized hydrophilic composite material to heat, a flushing inert gas, or heat and a flushing inert gas, thereby expelling $CO_2$ from the switchable moiety and rendering the composite material neutral and hydrophobic; and optionally, separating the neutral and hydrophobic composite material from the mixture.

In accordance with another embodiment, there is provided a method wherein the aqueous liquid contains water at concentrations 0.5-1 wt %, or alternatively 1-5 wt %, or alternatively 5-10 wt %, or alternatively >10 wt %.

In accordance with another embodiment, there is provided a method wherein exposing to heat is heating to 60° C., or alternatively 80° C., or alternatively 150° C.

In accordance with another embodiment, there is provided a method wherein the flushing inert gas is $N_2$, Ar, or air.

In accordance with another aspect of the application, there is provided uses of said composite materials for applications such as, but not limited to, removing water from non-aqueous solvents, removing water vapour from gaseous mixtures, and functioning as a cleanable surface for industrial reaction vessels and/or pipelines.

BRIEF DESCRIPTION OF THE FIGURES AND TABLES

For a better understanding of the present invention, as well as other aspects and further features thereof, reference is made to the following description which is to be used in conjunction with the accompanying drawings, where:

FIG. 1 depicts an embodiment of a switchable drying agent bead according to the present application, in which, in the presence of $CO_2$ some water is captured by chemical reaction, forming bicarbonate anions; some water is captured by adsorption to the bead; and some water is captured as waters of ion hydration; in the reverse direction, application of mild heating releases $CO_2$ and water from the bead;

FIG. 2 schematically depicts a process using a switchable drying agent to dry a non-aqueous liquid, removing the water-saturated drying agent, and subsequent regeneration of the drying agent;

Figure 19:
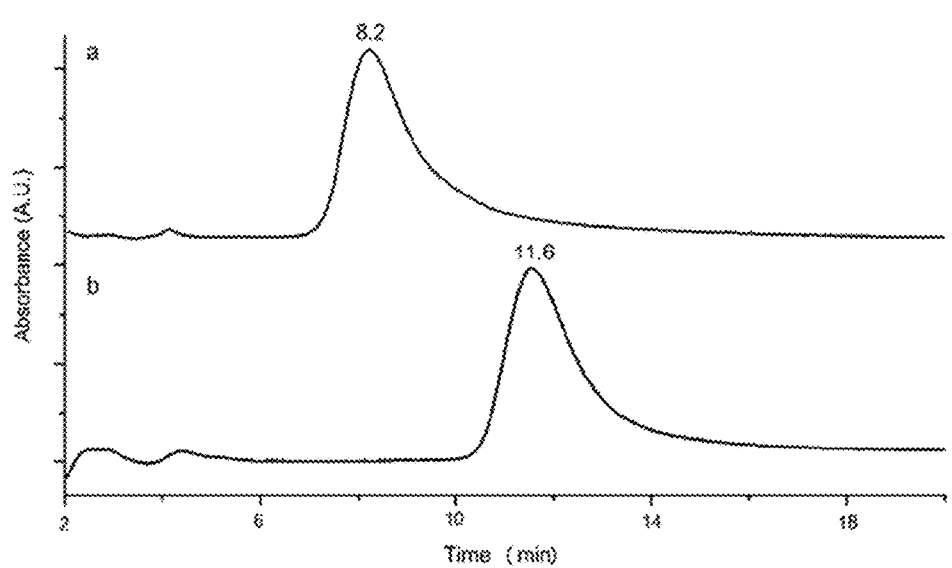
Figure 20:
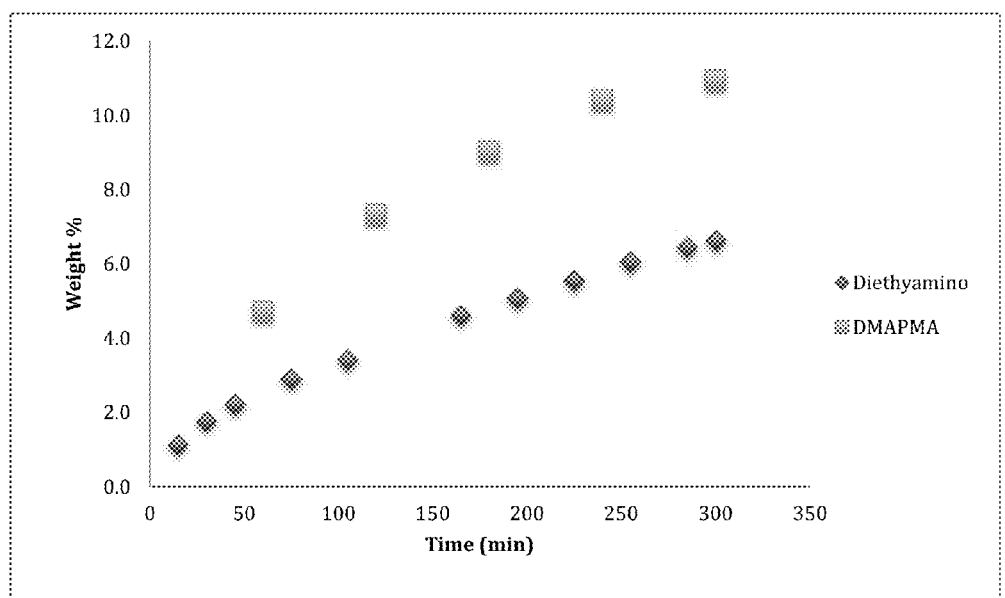
Figure 21:
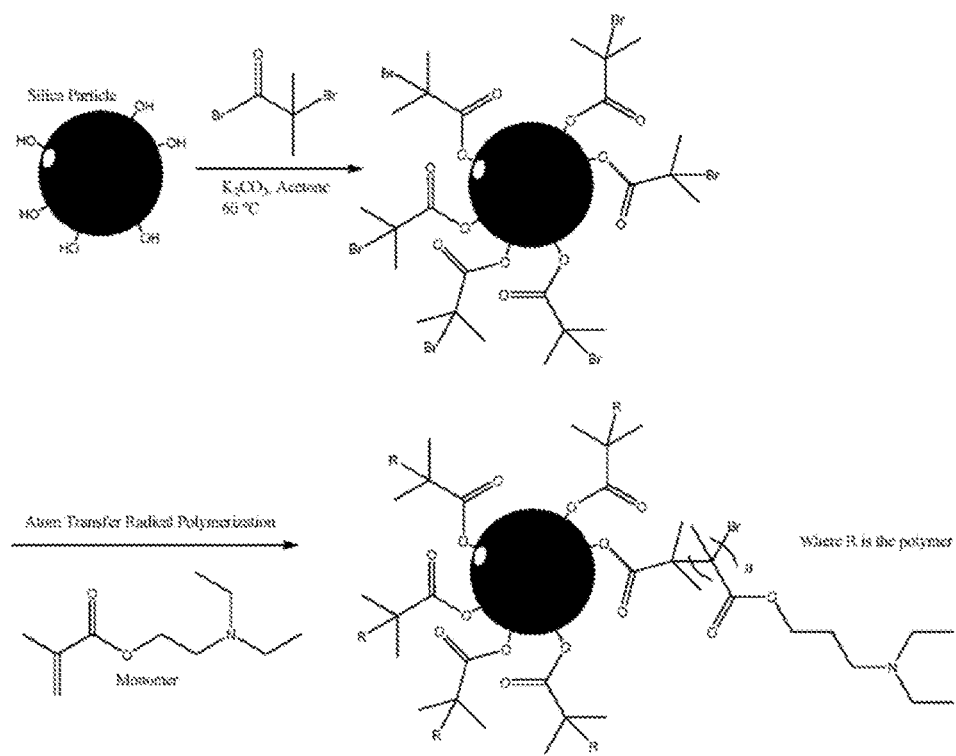
Figure 22:
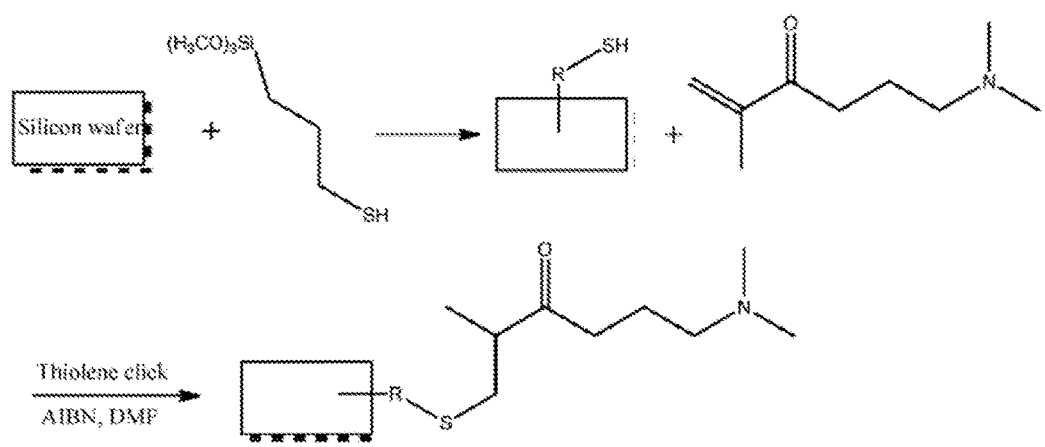
Figure 23:
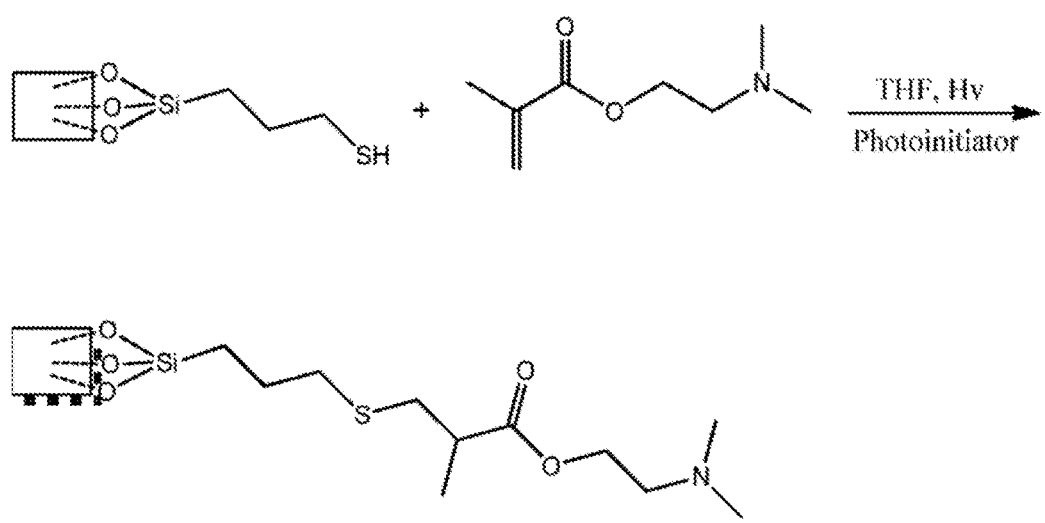
Figure 24:
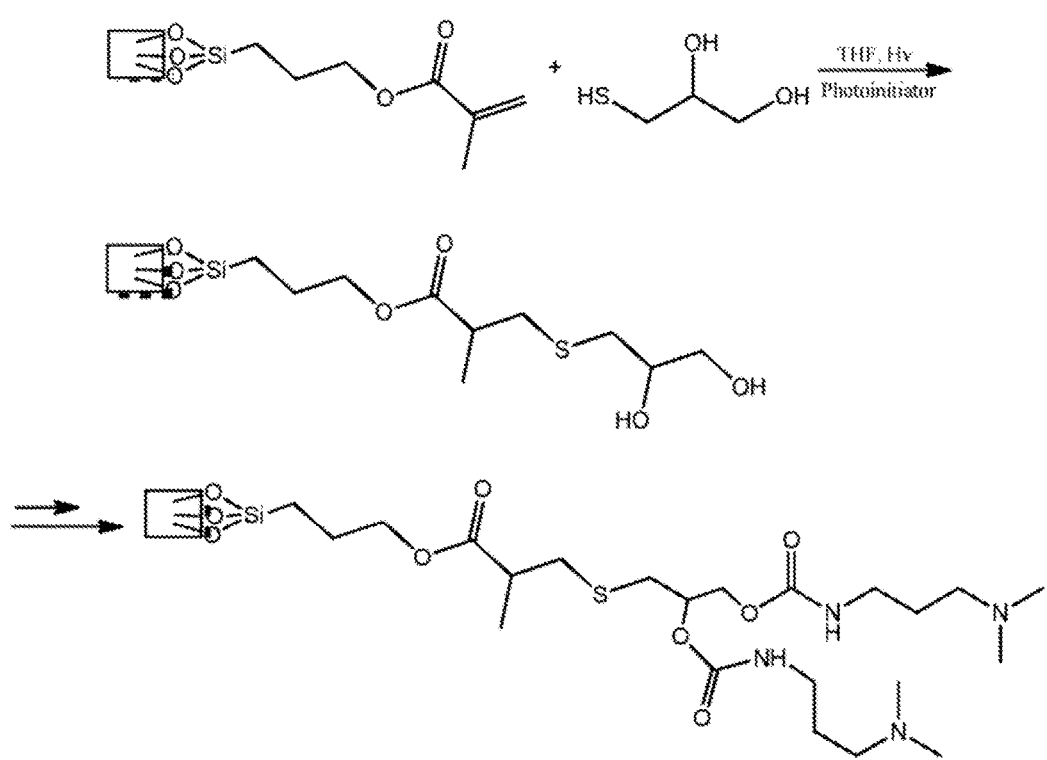
Figure 25:
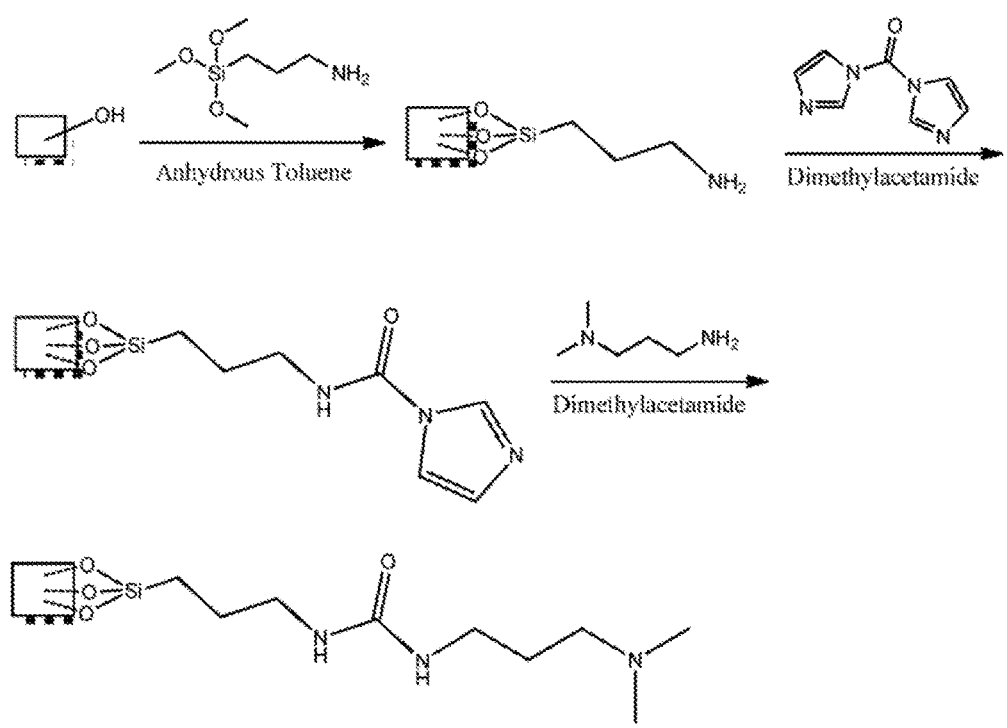
Figure 26:
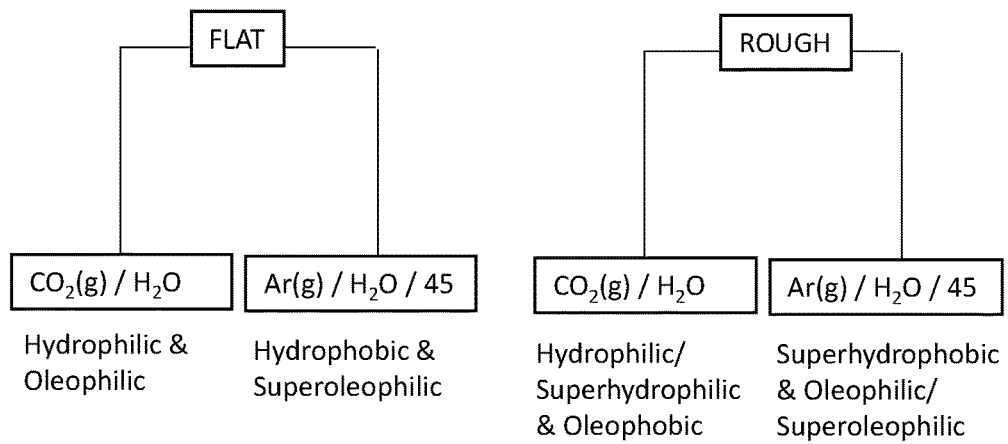
Figure 27:
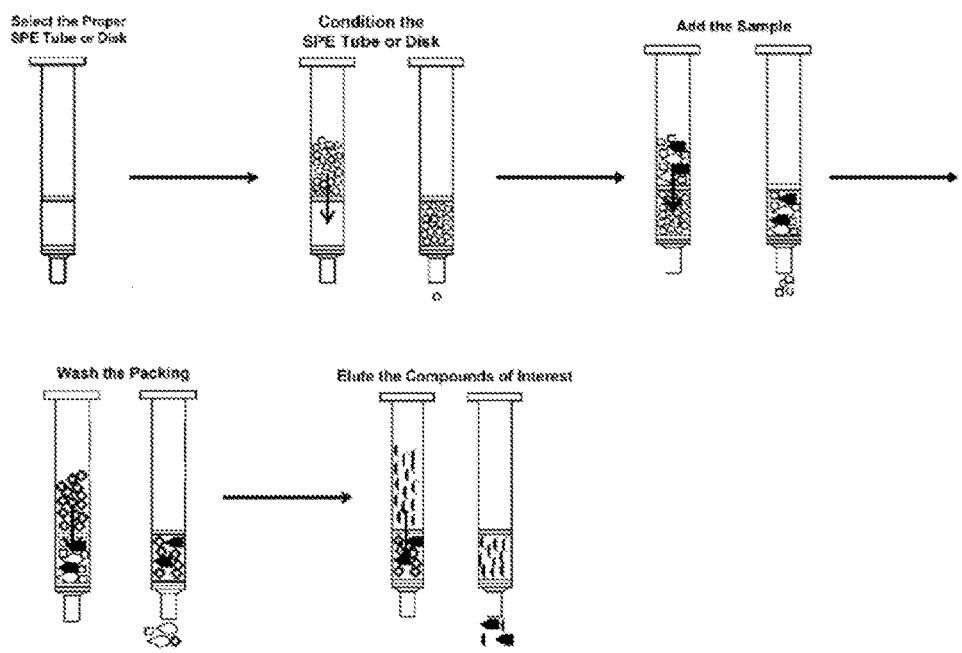

FIG. 19 depicts chromatograms of phenanthrene eluting off of a porous polymer monolith column: a) mobile phase without formic acid; b) mobile phase with 0.1% formic acid added); and FIG. 20 depicts particle weight percent saturation of commercially available 3-diethylam inopropyl functionalized silica particles (diethylamino) and herein described poly-DMAPMA functionalized silica particles (DMAPMA) due to exposure to wet $CO_2$;

FIG. 21 depicts SI-ATRP proof-of-concept investigation on silica particles;

FIG. 22 shows the synthesis of a 2+ component switchable surface;

FIG. 23 shows a surface bound molecule terminated with a thiol;

FIG. 24 shows a thiol based molecule used as a connecting group;

FIG. 25 depicts an example involving amide instead of ester linkages;

FIG. 26 depicts an example of super-hydrophobic and super-hydrophilic surfaces via functionalized-roughened surfaces; and FIG. 27 shows an example of switchable chromatographic supports for use in solid phase extraction (SPE).

Table 1 summarizes a comparison between three potential $CO_2$-switchable drying agents, three non-functionalized commercial drying agents, and their ability to remove water (5 wt % initially) from isobutanol solutions, and their performance upon subsequent regenerations and re-use (regeneration was performed by heating the drying agents at 50° C. for 4 h);

Table 2 summarizes results from drying isobutanol, doped with reduced water contents, using polymer beads;

Table 3 summarizes contact angle goniometry results for hydrophilic and hydrophobic forms of a library of silanes tested for $CO_2$ switchability;

Table 4 summarizes contact angle goniometry results from switching a N'-(6-mercaptohexyl)-N,N-dimethylacetimidamide self-assembled monolayer on gold between its hydrophobic and hydrophilic states over 3 cycles; and Table 5 summarizes elution times of phenol compounds separated via SPE using a switchable chromatographic support.

DETAILED DESCRIPTION

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, "switchable moiety" refers to a N-containing functional group that exists in a first form, such as a hydrophobic form, at a first partial pressure of $CO_2$, and, in the presence of water or other aqueous solutions, exists in a second form, such as a hydrophilic form, at a second partial pressure of $CO_2$ that is higher than the first partial pressure of $CO_2$. This term also applies to cases wherein COS, $CS_2$, or a mixture of any or all of $CO_2$, COS, or $CS_2$, is employed in place of $CO_2$ recited above.

As used herein, the term "unsubstituted" refers to any open valence of an atom being occupied by hydrogen. Also, if an occupant of an open valence position on an atom is not specified then it is hydrogen.

As used herein, "substituted" means having one or more substituent moieties present that either facilitates or improves desired reactions and/or functions of the invention, or does not impede desired reactions and/or functions of the invention. Examples of substituents include alkyl, alkenyl, alkynyl, aryl, aryl-halide, heteroaryl, cyclyl (non-aromatic ring), Si(alkyl)$_3$, Si(alkoxy)$_3$, halo, alkoxyl, amino, amide, amidine, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfamoyl, sulfonamide, nitro, nitrile, azido, heterocyclyl, ether, ester, silicon-containing moieties, thioester, or a combination thereof. Preferable substituents are alkyl, aryl, heteroaryl, and ether. Alkyl halides are known to be quite reactive, and are acceptable so long as they do not interfere with the desired reaction.

As used herein, "aliphatic" refers to hydrocarbon moieties that are linear, branched or cyclic, may be alkyl, alkenyl or alkynyl, and may be substituted or unsubstituted. "Aryl" means a moiety including a substituted or unsubstituted aromatic ring, including heteroaryl moieties and moieties with more than one conjugated aromatic ring; optionally it may also include one or more non-aromatic ring. "$C_5$ to $C_{10}$ Aryl" means a moiety including a substituted or unsubstituted aromatic ring having from 5 to 10 carbon atoms in one or more conjugated aromatic rings. Examples of aryl moieties include phenyl, biphenyl, naphthyl and xylyl.

As used herein, "alkyl" or "alkylene" refers to a linear, branched or cyclic, saturated or unsaturated hydrocarbon, which consists solely of single-bonded carbon and hydrogen atoms, which can be unsubstituted or is optionally substituted with one or more substituents; for example, a methyl or ethyl group. Examples of saturated straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl and 2-ethyl-1-butyl, 1-heptyl and 1-octyl. As used herein the term "alkyl" encompasses cyclic alkyls, or cycloalkyl groups.

As used herein, "cycloalkyl" refers to a non-aromatic, saturated monocyclic, bicyclic or tricyclic hydrocarbon ring system containing at least 3 carbon atoms. Examples of $C_3$-$C_n$ cycloalkyl groups include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

As used herein, "cycle" refers to an aromatic or nonaromatic monocyclic or bicyclic ring of carbon atoms, and which can be substituted or unsubstituted. Included within the term "cycle" are cycloalkyls and aryls, as defined above.

As used herein, "alkenyl" or "alkenylene" refers to a hydrocarbon moiety that is linear, branched or cyclic and comprises at least one carbon to carbon double bond which can be unsubstituted or optionally substituted with one or more substituents. "Alkynyl" or "alkynylene" refers to a hydrocarbon moiety that is linear, branched or cyclic and comprises at least one carbon to carbon triple bond which can be unsubstituted or optionally substituted with one or more substituents.

As used herein, "aryl" or "arylene" refers to hydrocarbons derived from benzene or a benzene derivative that are unsaturated aromatic carbocyclic groups from 5 to 100 carbon atoms, or from which may or may not be a fused ring system, in some embodiments 5 to 50, in other embodiments 5 to 25, and in still other embodiments 5 to 15. The aryls may have a single or multiple rings. The term "aryl" or "arylene" as used herein also include substituted aryls. Examples include, but are not limited to, phenyl, naphthyl, xylene, phenylethane, substituted phenyl, substituted naphthyl, substituted xylene, substituted 4-ethylphenyl, etc.

As used here in, "analyte(s)" refers to any solute(s) present in a mixture, and, in particular, to any solute(s) to be separated from the mixture. Use of the term 'analyte' in reference to chromatography is not intended to imply that the chromatographic techniques can only be used for analytical chromatography; rather the term 'analyte(s)' is equally intended to refer to solutes to be separated in preparative chromatography.

As used herein, "heteroaryl" refers to a moiety including a substituted or unsubstituted aryl ring or ring system having from 3 to 20, or 4 to 10 carbon atoms and at least one heteroatom in one or more conjugated aromatic rings. As used herein, "heteroatom" refers to non-carbon and non-hydrogen atoms, such as, for example, O, S, and N. Examples of heteroaryl moieties include pyridyl, bipyridyl, indolyl, thienyl, and quinolinyl.

As used herein, a "heterocycle" is an aromatic or non-aromatic monocyclic or bicyclic ring of carbon atoms and from 1 to 10, or 1 to 4, heteroatoms selected from oxygen, nitrogen and sulfur, and which can be substituted or unsubstituted. Included within the term "heterocycle" are heteroaryls, as defined above.

The term "switch/switched" means that physical properties have been modified. "Switchable" means able to be converted from a first form with a first set of physical properties, e.g., a hydrophobic form, to a second form with a second set of physical properties, e.g., a hydrophilic form, or vice-versa from the second state to the first state. A "trigger" is a change of conditions (e.g., introduction or removal of a gas, change in temperature) that causes a change in physical properties. The term "reversible" means that a reaction can proceed in either direction (backward or forward) depending on reaction conditions.

It should be understood, for the purposes of this application, that any switch that can be induced by $CO_2$ can also be induced by COS, $CS_2$, a combination thereof, or a mixture of $CO_2$ with any one of, or both of, COS and $CS_2$.

As used herein, "carbonated water" means a solution of water in which carbon dioxide has been dissolved, at any partial pressure.

As used herein, an "inert gas" means that the gas has insufficient carbon dioxide, $CS_2$ or COS content to interfere with removal of carbon dioxide, $CS_2$ or COS from a switchable moiety and/or a gas that has insufficient acidity to maintain a switchable moiety in its second, hydrophilic form. For some applications, air may be a gas that has substantially no carbon dioxide, $CS_2$ or COS and is insufficiently acidic. Untreated air may also be successfully employed, i.e., air in which the carbon dioxide, $CS_2$ or COS content is unaltered; this would provide a cost saving. For instance, air may be an insufficiently acidic gas that has substantially no carbon dioxide because in some circumstances, the approximately 0.04% by volume of carbon dioxide present in air is insufficient to maintain a switchable moiety in its second form, such that air can be a trigger used to remove carbon dioxide from a switchable moiety and cause switching.

As used herein, the term "hydrogen carbonate" refers to a switchable moiety's second form's counter ion, with a formula $[HCO_3]^-$ As used herein, "amidine" refers to a switchable functional group with a structure such as $X—N=CR^3NR^4R^5$, $R^3N=C(—X)NR^4R^5$, $R^3NH=CR^4N(—X)R^5$ where $R^3$ through $R^5$ are hydrogen or alkyl, alkenyl, alkynyl, aryl, or heteroaryl, each of which may be substituted, and X indicates a point of attachment. The second, ionic form of an amidine after exposure to carbon dioxide, $CS_2$ or COS is termed an "amidinium hydrogen carbonate".

As used herein, "amine" refers to a switchable functional group with a structure $—NR^1R^2$, where $R^1$ and $R^2$ are hydrogen or alkyl, alkenyl, alkynyl, aryl, or heteroaryl, each of which may be substituted. The second, ionic form of an amine after exposure to carbon dioxide, $CS_2$ or COS is termed an "ammonium hydrogen carbonate".

As used herein, "in presence of water" or "aqueous liquid" or variations thereof, means that at least a small amount of water is present, such as, but not limited to, 0.5-1 wt % water, or alternatively 1-5 wt %, or alternatively 5-10 wt %, or alternatively >10 wt %.

As used herein, "ionic" means containing or involving or occurring in the form of positively or negatively charged ions, i.e., charged moieties. "Neutral" as used herein means that there is no net charge. "Ionic salt" and "salt" as used herein are used interchangeably to refer to compounds formed from positively and negatively charged ions. These terms do not imply a physical state (i.e., liquid, gas or solid). It is important to note, however, that the terms "neutral form" and "ionic form" when used to refer to switchable materials do not refer to the overall ionized state of the material. As would be readily appreciated by a worker skilled in the art, the switchable material can comprise other functional groups that do not change their ionic state in response to the addition or removal of an ionizing trigger. Furthermore, in switching a switchable material, the material may not become fully ionized or neutralized at each switchable moiety by addition or reduction/removal of $CO_2$, respectively. However, the most fully ionized form, under the conditions used, is referred to herein as the ionic form and the most fully neutralized form is referred to herein as the neutral form.

As used herein, "hydrophobic" is a property of a switchable moiety or composite material that results in it repelling water. Hydrophobic moieties or materials are usually non-polar, and have little or no hydrogen bonding ability. Such molecules are thus compatible with other neutral and non-polar molecules.

As used herein, "hydrophilic" is a property of a switchable moiety or composite material that results in it attracting water. Hydrophilic moieties or materials are usually polar/ionized, and have a hydrogen bonding ability. Such molecules are thus compatible with other ionized/polar molecules.

As used herein, the term "contaminant" refers to one or more compounds that is intended to be removed from a mixture and/or surface and is not intended to imply that said contaminant has no value. For example, oil, which has significant value, may conveniently be called a contaminant when describing oil sands.

As used herein, the term "bond" or "bonded" refers to any covalent, ionic, coordination, physorbed bond, or any combination thereof.

As used herein, the term "polymer" or "polymeric material" refers to a macromolecule of moderate to high molecular weight, the structure of which is comprised of repeated monomer units, which are derived from molecules of low molecular weight; or, a material wherein the repeated monomer units form an extended lattice, such as, but not limited to, $SiO_2$.

As used herein, the term 'monolith' refers to a continuous solid material, as opposed to a discontinuous solid material such as separate particles, or a continuous liquid material, such as an eluting solvent.

As used herein, the term "copolymer" refers to a polymer, as defined above, composed of one or more structurally different monomeric repeat units.

As used herein, "drying" refers to removal of water from non-aqueous gaseous mixtures, non-aqueous liquid mixtures, and/or non-aqueous liquids, wherein the amount of residual water present can be large or small, such as, but not limited to, 0.5-1 wt % water, or alternatively 1-5 wt %, or alternatively 5-10 wt %, or alternatively >10 wt %.

The present application provides switchable materials, and methods of manufacture and uses thereof, for example as smart materials, which have stimuli-responsive properties. The present switchable materials can reversibly switch between a first form and a second form that differs from the first form by at least one physical and/or chemical property. In a preferred, but non-limiting example, the switchable material can reversibly switch between a hydrophobic form and a hydrophilic form upon application of external stimuli, such that they can be used, for example, as switchable drying agents and/or surfaces.

Responsive polymeric materials are known to reversibly switch their properties (e.g., wettability, viscosity, and adhesion) to adapt to external stimuli such as temperature, acid/base, oxidant/reductant, salt, light, as well as electric and magnetic fields [Stuart, M. A. C.; et al., *Nat. Mater.* 2010, 9, 101-113]. Porous polymer beads have been extensively used in ion exchange, chromatography, solid phase extraction and solid supported synthesis [Gokmen, T. G. et al., *Prog. Polym. Sci.* 2012, 37, 365-405]. Poly(2-(diethylamino)ethyl methacrylate), PDEAEMA, has been shown to form a pH-responsive surface, which reversibly switches between hydrophobicity/water repellency and superhydrophilicity [Stratakis, E., et al., *Chem. Commun.* 2010, 46, 4136-4138].

The external stimuli used to induce property changes in smart materials can strongly affect cost, environmental impact, and ease of switching for these materials. In comparison with other triggers, such as acids/bases, oxidants/reductants, salts, and light, inexpensive $CO_2$ is easily-removed (and, consequently, facilitates cycling between the two forms of the material), does not accumulate in a system, and is functional for non-transparent systems.

In accordance with an aspect of the present application, there is provided a composite material that is reversibly switchable between a first form and a second form, said composite material comprising a solid and solid-supported switchable moiety attached to said solid via a linker, wherein the switchable moiety comprises a functional group that is switchable between a neutral form associated with said first form of said composite material, and an ionized form associated with said second form of the composite material. In a specific embodiment, the linker is not a polyamine.

In accordance with another embodiment, there is provided a composite material which comprises the neutral form of the switchable moiety bound to a surface via a linker X as in the structure of formula 1,

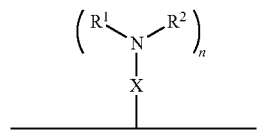

(1)

wherein:
NR$^1$R$^2$ is a switchable functional group, wherein R$^1$ and R$^2$ are each independently H, a C$_1$ to C$_{10}$ aliphatic group that is linear, branched, or cyclic, a C$_n$Si$_m$ group where n and m are independently a number from 0 to 10 and n+m is a number from 1 to 10, a C$_5$ to C$_{10}$ aryl group, or a heteroaryl group having 4 to 10 ring atoms, each of which may be substituted; or R$^1$ and R$^2$, together with the atoms to which they are attached, are connected to form a cycle, or heterocycle, each of which may be substituted;

n is an integer 1, 2 or 3; and

X is bonded to the solid and the switchable functional group and is a monovalent or a divalent moiety, such as carbonate, a substituted C$_1$-C$_{15}$ alkyl, C$_1$-C$_{15}$ alkylene, a substituted C$_{15}$-C$_{30}$ alkyl, C$_{15}$-C$_{30}$ alkylene, a substituted C$_1$-C$_{15}$ alkenyl, alkenylene, a substituted C$_{15}$-C$_{30}$ alkenyl, C$_{15}$-C$_{30}$ alkenylene, a substituted C$_1$-C$_{15}$ alkynyl, alkynylene, a substituted C$_{15}$-C$_{30}$ alkynyl, C$_{15}$-C$_{30}$ alkynylene, carbonate alkyl, C$_1$-C$_{15}$ carbonate alkylene, C$_{15}$-C$_{30}$ carbonate alkyl, C$_{15}$-C$_{30}$ carbonate alkylene, C$_1$-C$_{15}$ carbonate alkenyl, C$_1$-C$_{15}$ carbonate alkyenlene, C$_{15}$-C$_{30}$ carbonate alkenyl, C$_{15}$-C$_{30}$ carbonate alkenylene, C$_1$-C$_{15}$ carbonate alkynyl, C$_1$-C$_{15}$ carbonate alkynylene, C$_{15}$-C$_{30}$ carbonate alkynyl, C$_{15}$-C$_{30}$ carbonate alkynylene, aryl, arylene, heteroaryl, heteroarylene, thiol, silane, or siloxane, each of which may be substituted; or, X is a monovalent or a divalent cycle, or heterocycle, each of which may be substituted; optionally, X and R$^1$, X and R$^2$ or both, together with the atoms to which they are attached, are connected to form a cycle, or heterocycle, each of which may be substituted; and, wherein the alkylene, alkenylene and alkynylene moieties of X optionally comprise one or more amine, amide, ether, ester, thioether, thioester, silane, siloxane, or a combination thereof, within the hydrocarbon chain, and wherein when X is a monovalent moiety it is bound to the solid via a non-covalent interaction.

In a specific embodiment, the switchable moiety is bound to a surface via a spacer X as in the structure of formula 1a,

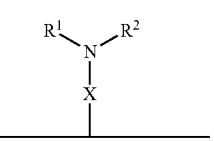

(1a)

In accordance with another embodiment, R$^1$ and R$^2$ of the structure of formula 1 are ethyl.

In accordance with another embodiment, there is provided a composite material which comprises the neutral form of the switchable moiety bound to a surface via a linker X as in the structure of formula 3a, or 3b, or 3c, or any rotational isomers thereof,

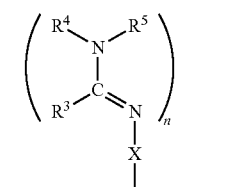

(3a)

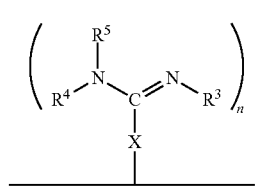

(3b)

-continued

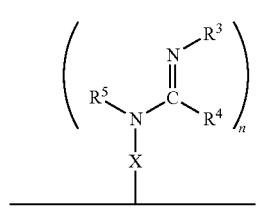

(3c)

wherein:
N=CR³NR⁴R⁵, R³N=CNR⁴R⁵, R³NH=CR⁴NR⁵ are each switchable functional groups, wherein $R^3$, $R^4$, and $R^5$ are independently H, a $C_1$ to $C_{10}$ aliphatic group that is linear, branched, or cyclic; a $C_nSi_m$ group where n and m are independently a number from 0 to 10 and n+m is a number from 1 to 10, a $C_5$ to $C_{10}$ aryl group, or a heteroaryl group having from 4 to 10 carbon atoms in the aromatic ring, each of which may be substituted; or, any combination of $R^3$, $R^4$, and $R^5$, together with the atoms to which they are attached, are connected to form a cycle, or heterocycle, each of which may be substituted;
n is an integer 1, 2 or 3; and
X is bonded to the solid and the switchable functional group and is a monovalent or a divalent moiety, such as a substituted $C_1$-$C_{15}$ alkyl, $C_1$-$C_{15}$ alkylene, a substituted $C_{15}$-$C_{30}$ alkyl, $C_{15}$-$C_{30}$ alkylene, a substituted $C_1$-$C_{15}$ alkenyl, alkenylene, a substituted $C_{15}$-$C_{30}$ alkenyl, $C_{15}$-$C_{30}$ alkenylene, a substituted $C_1$-$C_{15}$ alkynyl, alkynylene, a substituted $C_{15}$-$C_{30}$ alkynyl, $C_{15}$-$C_{30}$ alkynylene, aryl, arylene, heteroaryl, heteroarylene, thiol, silane, or siloxane, each of which may be substituted; or, X is a monovalent or a divalent cycle, or heterocycle, each of which may be substituted; optionally, X and one or two of $R^3$, $R^4$, and $R^5$, together with the atoms to which they are attached, are connected to form a cycle, or heterocycle, each of which may be substituted; and, wherein the alkylene, alkenylene and alkynylene moieties of X optionally comprise one or more amine, amide, ether, ester, thioether, thioester, silane, siloxane, or a combination thereof, within the hydrocarbon chain,
and wherein when X is a monovalent moiety it is bound to the solid via a non-covalent interaction.

In a specific embodiment, the material comprises the neutral form of the switchable moiety bound to a surface via a spacer X as in the structure of formula 3'a, or 3'b, or 3'c, or any rotational isomers thereof,

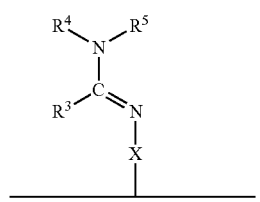

(3'a)

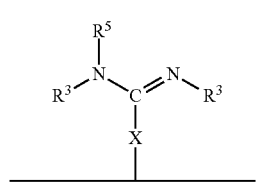

(3'b)

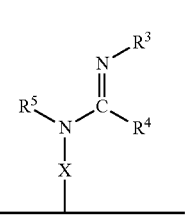

(3'c)

In accordance with another embodiment, $R^3$, $R^4$, and $R^5$ of the structure of formula 3a, or 3b, or 3c, 3'a, or 3'b, or 3'c or any rotational isomers thereof, are methyl.

In accordance with another embodiment, there is provided a composite material which comprises the ionized form of the switchable moiety bound to a surface via a spacer X as in the structure of formula 2 or 2a,

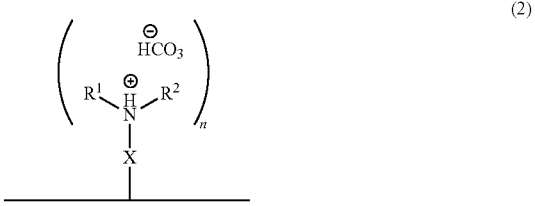

(2)

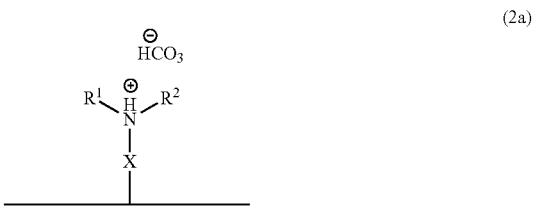

(2a)

wherein X, n, $R^1$ and $R^2$ are as defined above.

In accordance with another embodiment, there is provided a composite material which comprises the ionized form of the switchable moiety bound to a surface via a spacer X as in the structure of formula 4a, or 4b, or 4c, or 4'a, or 4'b, or 4'c, or any rotational isomers thereof,

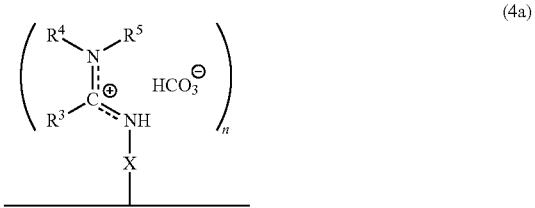

(4a)

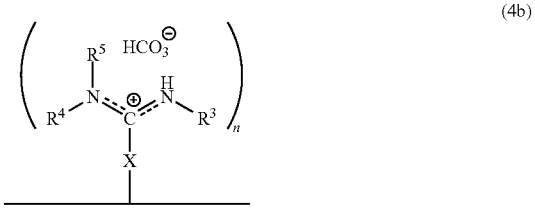

(4b)

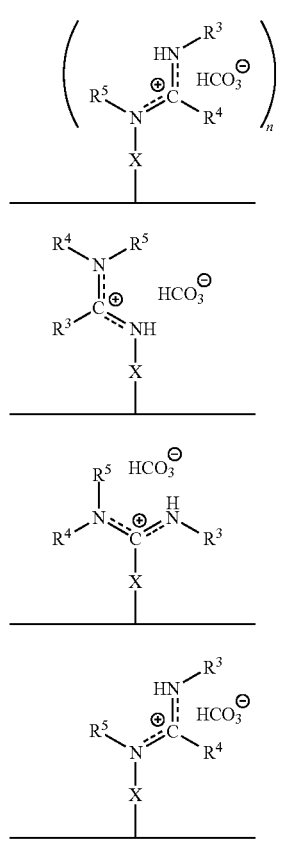

wherein the substituents X, n, $R^3$, $R^4$, and $R^5$ are as defined above.

In accordance with one embodiment, the switchable material is an effective switchable drying agent that reversibly switches between a desiccant form that captures water and a non-desiccant form that releases water. The desiccant form captures water by a process that comprises a chemical reaction rather than by physical adsorption alone. As a result, the present switchable desiccant can perform bulk water removal, similar to current inorganic salt desiccants, and yet be recyclable, similar to molecular sieves.

Typically, the present switchable materials rely on the known, readily reversible, reaction of water with an acid gas, such as $CO_2$, $COS$, $CS_2$, or a mixture thereof, that allows it to bind to amines, amidines and related compounds. Equation 1 shows the reaction of an amine and water and $CO_2$:

$$NR_3 + H_2O + CO_2 \rightarrow [NR_3H^+][HCO_3^-] \quad \text{(Eq. 1)}.$$

Although the present application typically refers to the use of $CO_2$ gas as the external stimulus, or trigger, to switch a material from its first form to its second form, it should be understood that the $CO_2$ can be replaced with another acid gas, such as $COS$, $CS_2$, or a mixture of acid gases. Equation 1 shows the reaction with $CO_2$, however, the analogous reaction readily occurs with other acid gases. In the case where the acid gas is $COS$ or $CS_2$ the product of the reaction would be the protonated amine as a salt with a sulfur substituted bicarbonate analogue.

Removal of the $CO_2$ trigger (or other acid gas or mixture thereof), completely or to an amount insufficient to maintain or convert the switchable material to its second form, will trigger a switch of the material back to its first form. This trigger can be, for example, a flushing gas, heat, agitation, or a combination thereof. The flushing gas can be air or an inert gas.

The presently provided composite materials comprise a solid material with a solid-supported switchable moiety bound thereto. In some instances the switchable moiety forms part of the solid material, such as, for example when the solid material is a functionalized polymer or the switchable moiety forms part of the backbone of a polymer.

Ideally the polymer contains amine, amidine or guanidine groups that are of sufficient basicity to be largely protonated by carbonated water at any $CO_2$ partial pressure applied during an application. For example, if the application involves exposure of the polymer to otherwise pure carbonated water, at 1 bar of $CO_2$ partial pressure, the polymer's basic sites would preferably have a $pKa_H$ of at least 9. The $pKa_H$ minimum would be different if the application used a different partial pressure of $CO_2$; or, if the carbonated water was gaseous (i.e., a gaseous mixture comprising $CO_2$ and water vapour) or a liquid mixed with a non-aqueous liquid.

Typically the amine group is not a pyridine or aniline derivative because of their inadequate basicities. However, an aniline derivative can be feasible when (i) a system uses $CO_2$ partial pressures significantly above 1 bar, (ii) the system is either at a neutral or somewhat acidic pH before $CO_2$ addition, or (iii) the system is at a pH<5.2 after $CO_2$ addition. In a system where pH does not go below 5.2 upon $CO_2$ addition, an aniline or pyridine group will not undergo sufficient protonation to obtain a significant change in physical properties, such as, but not limited to, hydrophilicity. However, pyridine, aniline, and imidazole groups, and/or other groups that have a lower basicity than trialkylamines, have a lower enthalpy of protonation. This lower enthalpy would result in a lower energy requirement, and potentially greater rate for converting the functional group between its hydrophilic ionic form and hydrophobic neutral form. Polymers that contain very basic sites (e.g., those with $pKa_H$ values above 13) are usually not preferred because more energy is required to reverse their protonation and remove water. Also, they are not usually preferred because, in most aqueous solutions, these basic sites would be largely protonated by water even in the absence of added acidic components. Polymers that have very high surface areas are preferred for applications in which a large number of surface protonatable sites are required. Such applications can include capturing of water from gases, or liquids, or use of switchable smart materials as filtering or chromatographic agents.

In alternative embodiments, the solid material to which the switchable moiety is bound is a metal, glass, or other solid support.

For many applications, choice of support material will be dictated by the application. For example, where transparency is required, a glass or transparent polymer would be preferred. Where great strength is required, a metal may be preferred. Where resistance to chemical dissolution by a non-aqueous solvent is required, glass or metal may be preferred over certain types of polymers; although, polymers known to have such resistance would also be acceptable. Where high surface area is required, a highly porous polymer, or other highly porous materials such as zeolites or mesoporous silicas, may be preferred. In many applications, the surface switchable moieties would not interfere or significantly modify properties of the bulk material, such as transparency, strength, insolubility, etc., although the material's porosity and surface area may be affected by addition of switchable moieties.

Figure 1:
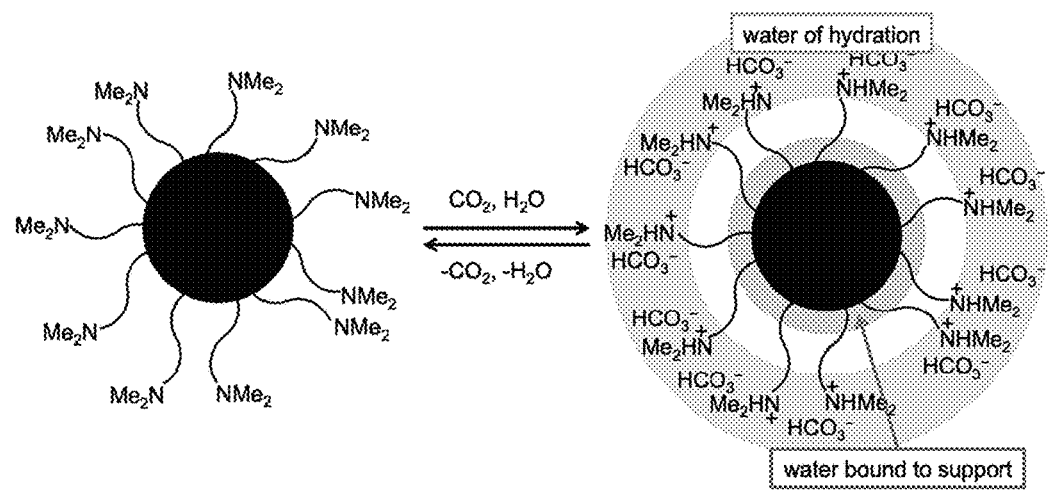

The present application provides switchable materials, such as switchable drying agents, that are composed of porous, amine and/or amidine functionalized polymers that respond to exposure to external stimuli, such as $CO_2$, COS, and/or $CS_2$. These materials are "switchable" between a hydrophobic form and a hydrophilic form by adding or removing $CO_2$, COS, and/or $CS_2$ (FIG. 1). COS or $CS_2$ are known to behave similarly to $CO_2$ and, thus, the switchable drying agents' external stimuli can be pure or impure $CO_2$, COS, $CS_2$, or any combination thereof. $CO_2$ in the absence of COS or $CS_2$ is preferred due to its low toxicity. However, COS or $CS_2$ may already be present in certain applications, either in addition to, or in the absence of $CO_2$. If COS and/or $CS_2$ are present in addition to $CO_2$, it may be more time and/or cost effective to retain the gases, or to use their presence to supplement $CO_2$'s ability to trigger a switch. In applications where COS and/or $CS_2$ are present in the absence of $CO_2$, either gas (or combination thereof) could then be used to trigger a switch. However, the use of $CO_2$ is preferred because combining a base, water, $CS_2$ and/or COS can lead to $H_2S$ production, which can introduce toxicity concerns.

Switchable Particles

Figure 2:
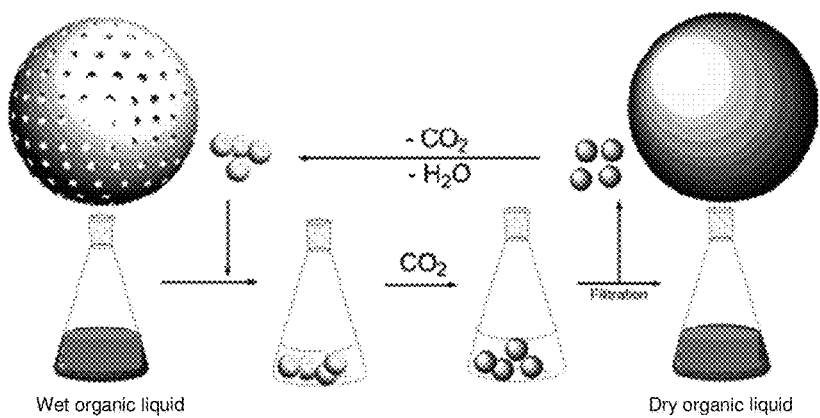

Switchable polymer particles (beads) can be used to remove water from non-aqueous liquids via a process similar to that performed using conventional desiccants. Additionally, these particles can be used to remove water vapour from gases, such as industrially produced methane/natural gases, where water might promote undesired clathrate solid formation; or, in $CO_2$ gas production, where water might promote corrosion of pipes or equipment. Once water is chemically or physically bound to the switchable drying agent, it can be removed from the non-aqueous liquid by mechanical separation, such as filtration, centrifugation or the like (FIG. 2). Regenerating a switchable drying agent is less energy-intensive than regenerating molecular sieves; switching the drying agent into a material that can no longer bind water merely requires moderate heating and/or flushing it with an inert gas. Subsequently, water is released and the drying agent can be reused.

Switchable Surfaces

Switchable surfaces are useful as smart materials for many of applications, some of which include industrial applications such as cleaning reaction vessels and/or pipelines that have otherwise become less efficient and/or hinder reactions due to chemical residue build-up. If a reaction vessel and/or pipeline were coated with a switchable surface, the vessel/pipeline can be effectively cleaned by simply applying an external stimulus. In one example, the switchable surface can switch between a hydrophobic and a hydrophilic form. Only molecules of like properties will adhere to the vessel/pipeline's walls; for example, only hydrophobic molecules (e.g., oil residues or tar, in which $CO_2$ is soluble) stick to a vessel/pipeline wall when the switchable surface is in its hydrophobic form. With application of the appropriate stimulus, the surface switches from its hydrophobic form to its hydrophilic form, and all hydrophobic molecules that were previously adhered to the wall are forced off. Once clean, the surface can be switched back to its hydrophobic form, and reactions/transportation of materials can continue.

Additionally, super-hydrophobic materials can be adapted for use as switchable surfaces. Super-hydrophobic materials can become less effective due to contamination from oils and other hydrophobic materials. If these super-hydrophobic materials switch their properties between a super-hydrophobic/super-oleophilic surface to a super-hydrophilic/super-oleophobic surface, surface contaminants can be readily removed or washed away. Once clean, the surface can be switched back to its super-hydrophobic/super-oleophilic surface for further use.

In one example, the switchable surface responds to $CO_2$, to a flushing inert gas, and/or to heat as external stimuli. In an industrial application of such a switchable surface, both $CO_2$ and heat can be captured from waste streams of other processes, allowing a repurposing of the waste heat and $CO_2$. Other smart materials that use light or pH to switch, instead of $CO_2$, can be used industrially, but would require retrofitting reaction vessels to facilitate light exposure, or would generate excessive amounts of waste for stabilizing pH. Such smart materials can be problematic because application of the required stimuli must be held constant in order to favour a select property to be obtained. While use of $CO_2$ as an external stimulus does cause a pH change, it is distinct from other methods of achieving a pH change (addition of acids/bases); the pH change it induces can be readily reversed by removal of $CO_2$, rather than by addition of a counteracting base.

Switchable Chromatography Support

In an alternative application, the switchable material can be used as a chromatographic support. This embodiment is particularly useful when the switchable material is a switchable particle that can be packed in a column using techniques already well established for standard chromatographic supports. By cycling the column with a $CO_2$ trigger and with a flushing gas and/or air and/or heat trigger, it is possible to cycle the switchable material in the column between its first and second forms. By varying the amount of $CO_2$ trigger in the eluting solvent, it is possible to vary the hydrophilicity of the support material over time, or over the length of the chromatographic column.

One chromatographic application wherein a switchable material may be used includes supercritical fluid chromatography (SFC). SFC is a chromatographic technique similar to high performance liquid chromatography (HPLC), but differs in that any eluting or mobile phase is a supercritical fluid (e.g., supercritical $CO_2$ "$scCO_2$"). As in HPLC, a SFC sample is introduced to a chromatograph via syringe injection, after which it is dissolved by $scCO_2$ and carried through a column where certain analytes are retained (i.e., bound to a stationary phase) more than others. Detection often occurs via UV/vis spectroscopy, but can also occur via mass spectrometry (MS), light scattering, or flame ionization detection (FID). This method can be used as an analytical method, or as a preparative separation. In either case, use of $scCO_2$ can reduce amounts of organic solvent needed for chromatographic analysis, as compared to liquid chromatography (LC) or HPLC. In this case, varying the amount of water in the eluting solvent will alter the hydrophilicity of the switchable material. Varying the amount of water in the eluting solvent will result in a variation in the hydrophilicity of the support over time, or over the length of the column.

If a column's packing material (stationary phase), or a column's walls comprise a switchable surface group(s), then, without wishing to be bound by theory, it would be expected that retention of analytes would be different if the switchable groups are either neutral or ionic. While $scCO_2$ can be very pure (99.99 or 99.999% pure), and therefore very dry, some amount of water vapour, or dissolved alcohol, or other protic compound, can be deliberately added to the $scCO_2$ in order to generate acids in situ. These acids can protonate the switchable surface groups (e.g., amines), and convert them into an ammonium bicarbonate (in the case of water), or an ammonium alkyl carbonate (in the case of alcohols) with corresponding changes in retention behavior, and therefore elution time, of analytes. This change can be reversed if scCO$_2$ that does not contain a protic source is passed through the column.

In an alternative embodiment, a column containing basic groups can be used in SFC to separate a mixture of alcohols: alcohols that form relatively stable alkyl carbonate ions upon interaction with scCO$_2$ and the column's basic groups would be retained longer on the column, and therefore elute more slowly than alcohols that form less stable alkyl carbonate ions.

To gain a better understanding of the invention described herein, the following examples are set forth. It should be understood that these examples are for illustrative purposes only. Therefore, they should not limit the scope of this invention in any way.

EXAMPLES

General Methods 2,2'-Azobisisobutyronitrile (AIBN) was recrystallized from methanol. Other chemicals were used as received from commercial sources: 2,3-dibromo-1,4-butanediol (Aldrich, Milwaukee, Wis., 53233, USA); poly(vinyl alcohol) (Aldrich); dimethyl carbonate (Sigma-Aldrich, 3050 Spruce St. Louis, Mo., 63103, USA); potassium hydroxide (Sigma-Aldrich); diethylamine and triethylamine (Sigma-Aldrich); methacryloyl chloride (Alfa Aesar, 26 Parkridge Rd, Ward Hill, Mass. 01835, USA); magnesium sulfate (Sigma-Aldrich); basic alumina oxide (Sigma-Aldrich); 3-dimethylaminopropyl-functionalized silica (Sigma-Aldrich); mesoporous silica (Silicycle, 2500, Parc-Technologique Blvd, Quebec City, Quebec, G1P 4S6, Canada); Si(CH$_2$)$_n$N(CH$_3$)$_2$ (Silicycle, 2500, Parc-Technologique Blvd, Quebec City, Quebec, G1P 4S6, Canada); CO$_2$(g) (Praxair, 1 City Centre Dr. Mississauga, On. Canada L5B 1M2); 2-dimethylaminoethanol (Sigma-Aldrich); hydrochloric acid (Fisher Scientific, reagent grade); carbonyldiimidazole (Sigma-Aldrich); N,N-dimethylacetamide (Sigma-Aldrich); dimethylsulfoxide (Fisher Scientific); 1,1,3,3-tetramethylguanidine (Sigma-Aldrich); silicon wafer (N type, P dope, 100 mm (wafer size), SSP (single side polish), 325 um (thickness of thermally grown oxide layer), test grade from university-wafer.com); and isobutanol (SAFC, P.O. Box 14508, St. Louis, Mo., 63178, USA). Contact angles were measured using a AST Products VCA Optima Goniometer. $^1$H and $^{13}$C NMR spectra were recorded using a Bruker Avance-400 spectrometer. Chloroform-d (D, 99.8%) was bought from Cambridge Isotope Laboratories, Inc. High resolution mass spectra were obtained using a Qstar XL QqTOF instrument with an ESI source. Thermogravimetic analysis (TGA) was performed using a TA Q-500 analyzer; sample was heated in a nitrogen atmosphere. Particle size was determined using a Malvern Mastersizer 2000 (size range from 0.05 to 2000 μm) equipped with a Hydro2000S optical unit. A Philips XL-30 ESEM FEG instrument was operated at 2 kV to obtain SEM images after samples were coated by Au. After sample was degassed at 140° C. for at least four hours, a nitrogen sorption isotherm was run on a Quantachrome Autosorb-1C at 77 K. Water concentrations within solutions was measured using a Perkin Elmer thermal conductivity detector on a Perkin Elmer Clarus 600 GC, with a SLB-IL107 fused silica capillary column.

Example 1: Synthesis of 1,4-bis(diethylamino)-2,3-butanediol

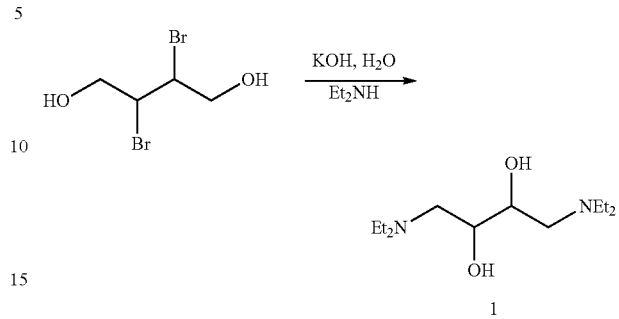

Potassium hydroxide (KOH (8.75 g, 0.151 mol) was dissolved in deionized water at 0° C. and diethylamine (25 mL, 0.242 mol) was added. After 10 min, 2,3-dibromo-1,4-butanediol (15.1 g, 0.0605 mmol) was added into the aqueous solution. The reaction mixture was kept stirring for 18 h and then heated up to 50° C. The reaction solution was kept at 50° C. overnight. When water and excess diethylamine was removed under reduced pressure, dimethyl carbonate (50 ml) was mixed with the residue, and any filtrate was collected. After removing dimethyl carbonate under reduced pressure, pure 1,4-bis(diethylamino)-2,3-butanediol was obtained (7.62 g, 54%). $^1$H NMR (400 MHz, CDCl$_3$): δ (ppm)=3.77 (t, 12H, J=5.7 Hz), 2.71-2.57 (m, 12H), 1.06 (t, 12H, J=7.1 Hz); $^{13}$C{$^1$H} NMR (100 MHz, CDCl$_3$): δ (ppm) 68.8, 56.4, 47.3, 11.6; HRMS (m/z): [M]$^+$ calcd. C$_{12}$H$_{28}$N$_2$O$_2$, 232.2151, found 232.2157.

Example 2: Synthesis of Crosslinkable Methylmethacrylate Monomer, 1,4-bis(diethylamino)-2,3-bismethacryoloxybutanoate

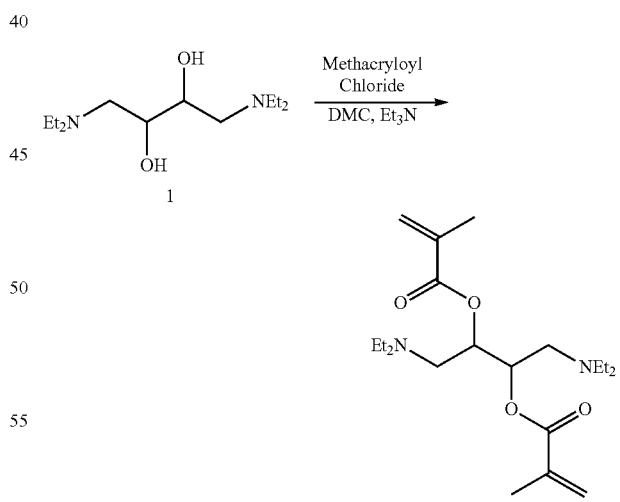

1,4-Bis(diethylamino)-2,3-butanediol (6.9 g, 30 mmol) and triethylamine (20 mL) in anhydrous dimethyl carbonate (DMC, 150 mL) were cooled to 10° C. under a nitrogen atmosphere. Methacryloyl chloride (7.2 mL, 74 mmol) in dimethyl carbonate (solvent, 50 mL) was added via a syringe. The reaction mixture was magnetically stirred overnight. A salt by-product was removed from the reaction mixture by filtration, and a product-containing filtrate was washed twice with water (purified with a Millipore Synergy Ultrapure Water Systems) to remove excess triethylamine. The non-aqueous phase was dried over magnesium sulfate ($MgSO_4$), and the mixture was filtered through a basic alumina column once the solvent was removed. The product remained as a pale yellow solid (8.9 g, 81%). $^1$H NMR (400 MHz, $CDCl_3$): δ (ppm)=6.15-6.00 (m, 2H), 5.51-5.49 (m, 2H), 5.30-5.24 (m, 2H), 2.60-2.37 (m, 12H), 1.87 (brs, 6H), 0.92 (t, 12H, J=7.1 Hz); $^{13}C\{^1H\}$ NMR (100 MHz, $CDCl_3$): δ (ppm)=166.1, 136.2, 125.4, 70.8, 52.3, 47.8, 18.1, 11.9; HRMS (m/z): [m]$^+$ calc. $C_{20}H_{36}N_2O_4$, 368.2675; found 368.2668. Anal. Calc. for $C_{20}H_{36.5}N_2O_{4.25}$: C, 64.40%; H, 9.86%; N, 7.51%. Found: C, 64.60%; H, 9.90%; N, 7.23%.

Example 3: Preparation of Polymer Beads Via Suspension Polymerization 1,4-Bis(diethylamino)-2,3-bismethacryoloxybutanoate (2.73 g, 7.4 mmol) and azobisisobutyronitrile (AIBN) (12 mg, 0.073 mmol) were dissolved in toluene (4 mL) with magnetic stirring; $O_2(g)$ was displaced from the mixture by bubbling $N_2(g)$ through the mixture.

Polyvinyl alcohol (87-89% hydrolyzed, average $M_w$ 124000-186000, 0.4 g) and water (40 mL) in a 250 mL round bottom flask were mechanically stirred with an overhead stirrer at 300 RPM and bubbled with $N_2(g)$ until the polymer was dissolved. Once the non-aqueous solution containing 1,4-bis(diethylamino)-2,3-bismethacryoloxybutanoate and AIBN was added to the aqueous polyvinyl alcohol solution, the mixture was bubbled with $N_2(g)$ and heated to 80° C. After 4 h at that temperature, the mixture was cooled down under ambient conditions and filtered through a Buchner funnel under vacuum. Polymer beads were washed three times with water (purified with a Millipore Synergy Ultrapure Water Systems), which was heated to 50° C., and dried at 100° C. under vacuum. Yield was 70%. Mean particle size was 220 μm (see FIG. 4).

Example 3A: Preparation of Polymer [3-(dimethylamino)propyl] Functionalized Mesoporous Silica Particles Mesoporous silica, type MCM-41 (0.3 g), was dried in an oven at 150° C. for 2 h. The MCM-41 was added to toluene (50 mL) with magnetic stirring for 30 min. Water (0.2 mL, Millipore quality) was added to the magnetically stirred solution, after which the temperature was increased to 80° C. After reaching 80° C., (N,N-dimethylaminopropyl)trimethoxysilane (0.9 mL, 0.004 mol) was added to the mixture, which was magnetically stirred for 1 h. The silica was separated from solution via vacuum filtration using a glass frit. The silica was then washed, first with dichloromethane (200 mL), and then ethanol (500 mL). Residual solvent was removed by drying the silica in an oven at 100° C. for 3 h. Mean particle size was 300 μm.

Example 3B: Procedure for Testing Drying Agents Efficacy

Drying agent (500 mg) was added to isobutanol (10 g, 0.5 wt %, or 1 wt % or 5 wt % water) into a vial. The mixture was magnetically stirred while $CO_2$ was bubbled through it using a dispersion tube. After 1 h, $CO_2$ bubbling was stopped; the vial was capped and allowed to stir for 16 h. The drying agent was removed from the isobutanol via vacuum filtration using a Hirsch funnel. Water content remaining in the isobutanol was measured via gas chromatography coupled to a thermal conductivity detector (GC-TCD).

Example 3C: Heat Cost Per Gram of Water Removed from Molecular Sieves and the Cross-Linked Polymer Beads 1) Calculate heat cost to regenerate drying agent per gram of sample:

Heat cost per gram of sample=enthalpy to remove water+energy to heat up drying agent to temperature of water release.

Figure 8A:
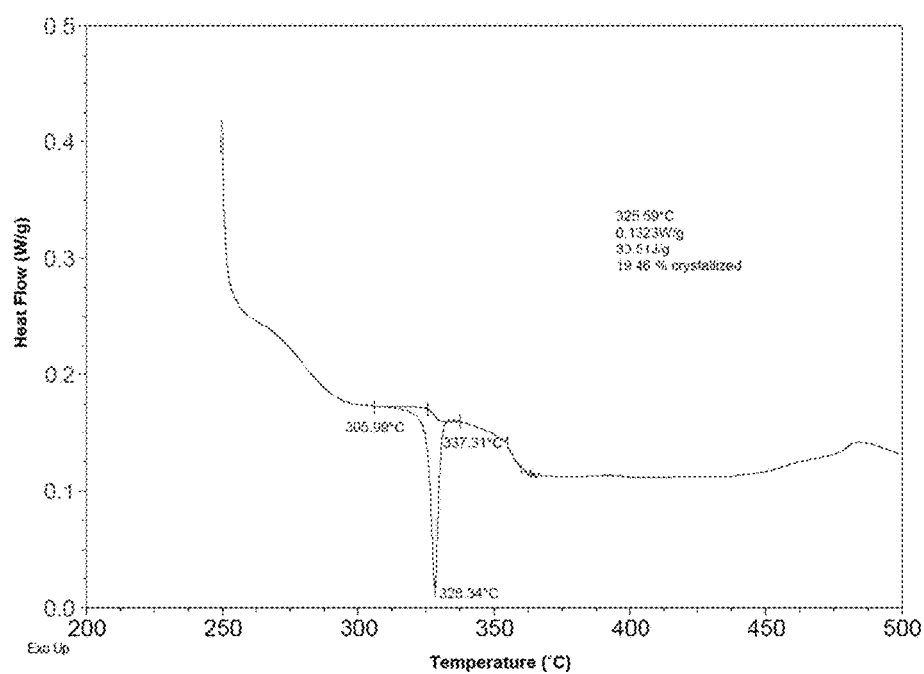
FIG. 8A depicts a differential scanning calorimetry (DSC) curve of regenerating wet molecular sieves. Y-axis is heat flow (normalized)(W/g), X-axis is T (° C.)
Figure 8B:
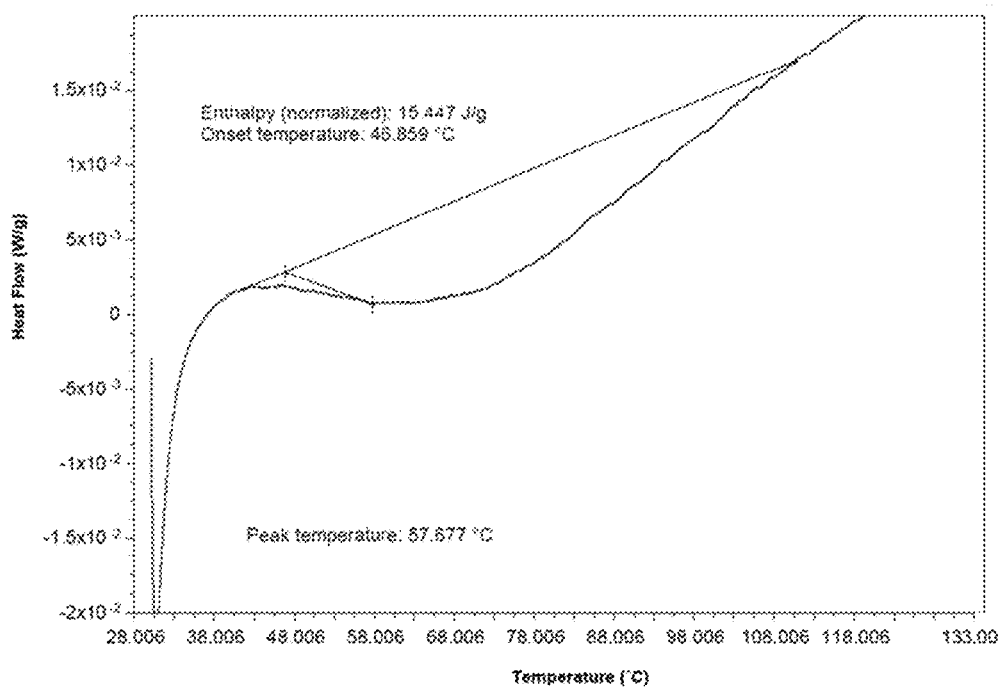
FIG. 8B depicts a differential scanning calorimetry (DSC) curve of regenerating switchable polymer beads. Y-axis is heat flow (normalized)(W/g), X-axis is T (° C.)

Integrating the DSC curves of FIGS. 8A and 8B provided enthalpy of drying agent regeneration for molecular sieves (30 J·g$^{-1}$) and for polymer beads (16 J·g$^{-1}$), wherein heat capacity of fused silica is 0.73 J·g$^{-1.°}$ C.$^{-1}$ [W. F. Beech, *J. Chem. Soc.* 1951, 2483] and poly(methyl methacrylate) is 1.42 J·g$^{-1.°}$ C.$^{-1}$ [B. T. Cho, N. Kim, Synth. Commun. 1996, 26, 2273]. Please note: heat capacity for PMMA was used here as an approximate substitute for the cross-linked polymer particles' unknown heat capacity.

It was found that molecular sieves must be heated to 325° C. to initiate water release, whereas the cross-linked polymer beads need to be raised to 50° C. to initiate water release. Therefore:

Heat cost to regenerate 'wet' mol. sieves=30 J·g$^{-1}$+ 0.73 J·g$^{-1.°}$ C.$^{-1}$×300° C.=249 J·g$^{-1}$ Heat cost to regenerate 'wet' pol particles=16 J·g$^{-1}$+ 1.42 J·g$^{-1.°}$ C.$^{-1}$×25° C.=52 J·g$^{-1}$ 2) Convert energy cost per gram of sample to per gram of water removed using the drying agent For molecular sieves, heat cost per gram of water=249 J·g$^{-1}$÷0.380 g of water removed per gram of drying agent=655 J·g$^{-1}$ For the polymer beads, heat cost per gram of water=52 J·g$^{-1}$÷0.380 g of water removed per gram of drying agent=137 J·g$^{-1}$ Examples 1-3C provides a polymer comprising amine moieties in its framework that can be used to generate porous switchable polymeric beads. While there are many heterogeneous polymerization methods available to produce porous polymer beads, inexpensive suspension polymerizations are easy to scale up for industrial applications; and generally, fully cross-linked polymers have large surface areas and provide better accessibility for guest molecules, such as water. Hence, a cross-linkable methylmethacrylate monomer, 1,4-bis(diethylamino)-2,3-bismethacryoloxybutanoate, (EXAMPLE 2) was designed and synthesized to produce the porous polymer beads containing switchable tertiary amine moieties.

Figure 3:
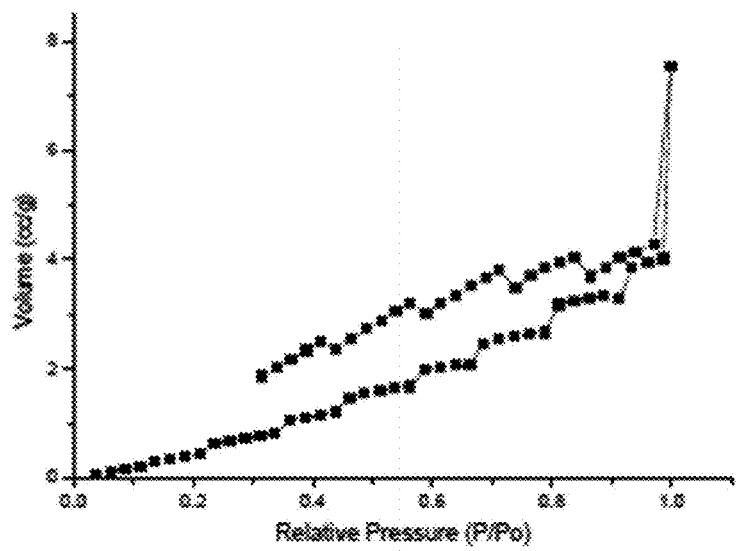
FIG. 3 depicts an isotherm for $N_2$ adsorption in porous switchable polymer beads at 77 K.
Figure 4:
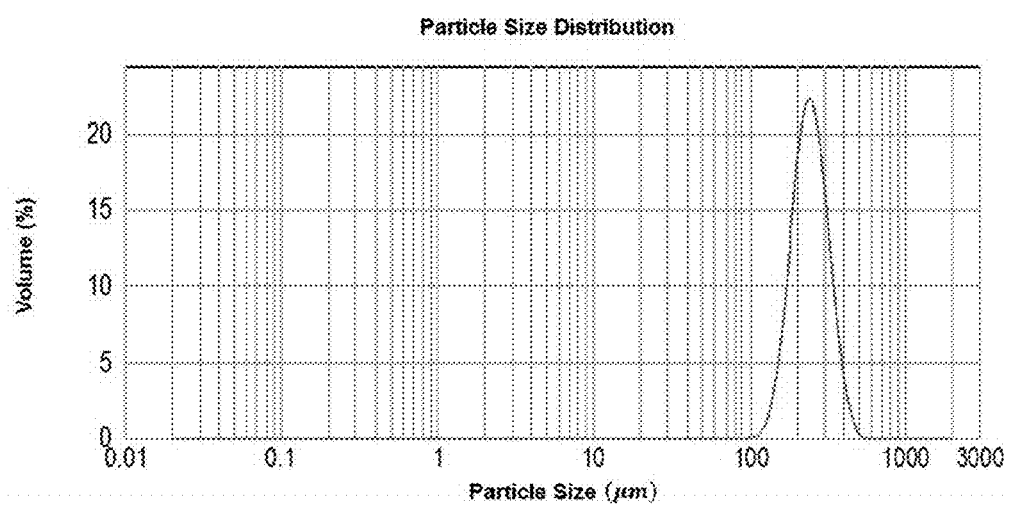
FIG. 4 depicts light scattering analysis for particle size of switchable polymer beads.
Figure 5:
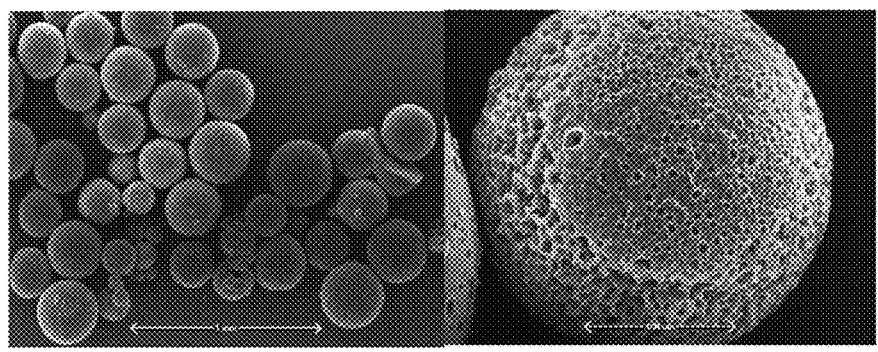
FIG. 5 depicts SEM images of porous switchable polymer beads.
Figure 6:
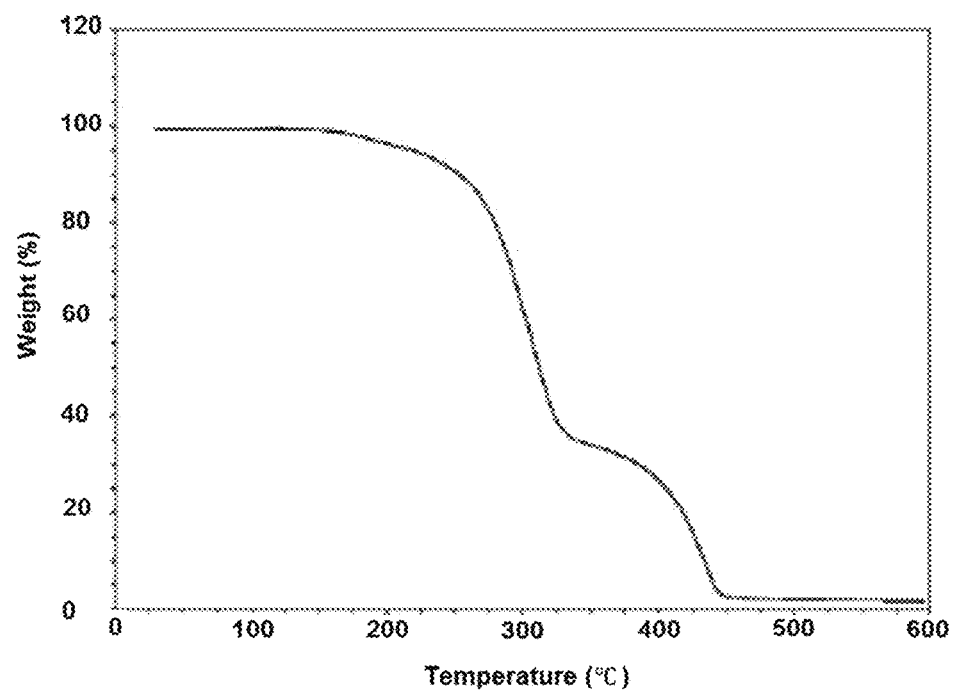
FIG. 6 depicts thermal gravimetric analysis of porous switchable polymer beads (rate of 10° C./min to 600° C.)

Suspension polymerization was employed to prepare porous polymer beads from the crosslinkable methylmethacrylate monomer described above. The polymer beads were characterized using isothermal $N_2$ adsorption (Brunauer-Emmett-Teller (BET) surface area), light scattering, scanning electron microscope (SEM) imaging, and thermal gravimetric analysis (TGA). BET surface area was found to be 40 m$^2$/g (FIG. 3), and average particle size was determined from light scattering to be ~220 μm (FIG. 4). Had these microspheres not been porous, their calculated surface area would have been 0.03 m$^2$/g; therefore, isothermal $N_2$ adsorption was indicative of the fact that the polymer beads were porous. SEM imaging demonstrated micrometer-level porosity (FIG. 5), while TGA analysis confirmed that the porous polymer beads were thermally stable at temperatures <200° C. (FIG. 6).

The porous polymer beads, made from the above cross-linkable methylmethacrylate monomer, [3-(dimethylamino) propyl]-functionalized mesoporous silica particles (pore size: 10 nm, prepared according to the literature procedure in Sharma, Krishna K.; et al., Angewandte Chemie International Edition. 2007, 119(16), 2937-2940), and commercially available 3-dimethylaminopropyl-functionalized silica gel were studied as potential switchable drying agents. Titrations with hydrochloric acid, monitored with a pH electrode, (Thermo Electron Corporation Orion 4 Star pH Conductivity Benchtop) indicated that accessible amine moieties for the polymer beads, amino-functionalized mesoporous silica and commercial silica gel were 2.6 mmol/g, 1.5 mmol/g and 1.7 mmol/g respectively. Higher accessible amine content in the porous polymer beads was designed to help reversibly capture more water molecules.

To evaluate water-removal performance of each contending switchable drying agent, the polymer beads, mesoporous silica, and silica gel were immersed in wet isobutanol (5 wt % water in isobutanol), exposed to $CO_2$ via bubbling for 1 h, and stirred overnight in a sealed vial (15 h). Water concentration in the isobutanol was monitored using gas chromatography coupled to a thermal conductivity detector (GC-TCD) to determine the water content [Jayawardhana, D. A.; et al., LCGC North America 2012, 2 (30)]; drying performance results were summarized in Table 1. The polymer beads showed a greater ability to capture water (Table 1, row 3), consistent with having a greater accessible nitrogen content. Their efficacy decreased with continued recycling, unlike the silica based drying agents; however, upon increasing $CO_2$ bubbling time to 3 h, the polymer beads remove more water per gram of polymer beads and maintain their drying ability through several cycles (Table 1, 4th row).

Figure 7:
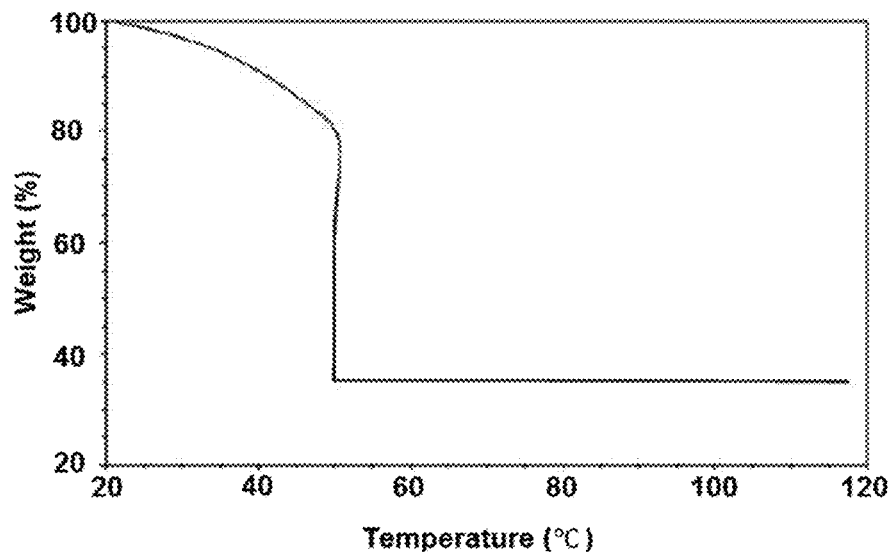
FIG. 7 depicts scanning thermal gravimetric analysis (TGA) graph for evaluation of switchable polymer bead regeneration (rate of 2° C./min to 50° C., isothermally at 50° C. for 4 h, then increased to 120° C.)

Regeneration temperatures for the polymer beads were also established. After using the switchable polymer beads to dry wet isobutanol (see above), a TGA experiment was performed where the beads where heated isothermally at 50° C. for 4 h, and then heated to 120° C. As shown in FIG. 7, a weight loss process was observed initially (up to 50° C.), but no further weight loss was observed upon additional heating at 120° C. This demonstrated efficient regeneration of the polymer beads by heating at 50° C. for 4 h.

The polymer beads were also compared to molecular sieves, unfunctionalized silica, and unfunctionalized alumina, which are known reusable drying agents. Silica and alumina were activated by heating each absorbent to 250° C. for 24 h before being added to a wet isobutanol solution. The same procedure was then followed as described above for the switchable desiccants, but in the absence of $CO_2$. As illustrated in Table 1, both the polymer beads and molecular sieves were effective drying agents for one cycle, but only the polymer beads remained effective after regeneration at 50° C. The unfunctionalized alumina and silica removed less water than the polymer beads or the molecular sieves, but continued to function at this lower level for multiple cycles. A possible explanation for the reduced recyclability of molecular sieves is that not enough thermal energy was supplied during the regeneration step to fully release water after use.

To test this, differential scanning calorimetry (DSC) was used to compare energy required to release water from each drying agent after one cycle (FIGS. 8A and 8B). Heating the polymeric beads to the regeneration temperature of 50° C. required ca. 36 J per g of beads compared to 325° C. and 219 J/g for molecular sieves (Example 3C). Once at the regeneration temperature, the polymeric beads required 16 J per g of particles to desorb water, according to DSC measurements, compared to 30 J/g for molecular sieves. Including both energy costs, the total energy requirement per gram of captured water is 140 J/g for the polymeric beads and 660 J/g for the molecular sieves. Although this comparison is an approximation and not for optimized systems, it highlights an advantage of using switchable drying agents rather than molecular sieves, in terms of lower energy requirements for regeneration. In comparison to unfunctionalized silica and alumina, the porous polymer beads are better in terms of the amount of water removed per g of drying agent, but comparable in terms of ease of regeneration.

To evaluate the beads' ability to dry isobutanol having a lower initial water content, two further experiments were performed using isobutanol doped with less water. The beads were able to reduce water content of solutions containing 1 wt % $H_2O$, to a value of 0.8 wt %, but did not remove water from solutions containing only 0.5 wt % $H_2O$. A lower limit for the polymer beads to dewater isobutanol was therefore determined to be slightly less than 1 wt % $H_2O$, but not as low as 0.5 wt % $H_2O$. Not wishing to be bound by theory, it is expected that increasing the nitrogen-containing functional group's basicity, such as by using amidine groups, would increase the drying agent's ability to dry solvents to a lower level of residual water.

Further, as it was recognized that solvent retention would be undesirable, amounts of isobutanol retained by the polymer beads was examined. A known amount of used drying agent was added to $D_2O$ and acidified with HCl. The acid was assumed to liberate any species necessarily associated with the nitrogen atoms through protonation. After the sample was stirred for 2 h, the amount of isobutanol present in solution was quantified by integrating signals present in a $^1$H-NMR spectrum against an internal standard (see FIG. 11). This showed that the mass of water retained on the polymer beads is 1.3× greater than the amount of isobutanol, suggesting that the polymer beads preferentially bind water. As the used drying agent particles were obviously physically wet with the solvent from which they were recovered, it was not surprising that isobutanol was detected.

One embodiment of the foregoing is use of switchable desiccants to dry gaseous $CO_2$, liquid $CO_2$, and/or gaseous mixtures containing significant amounts of $CO_2$, such as, but not limited to, flue gases or other gas streams from combustion, fermentation, decomposition, or mining processes. Such components and/or mixtures can be corrosive to metal equipment and/or pipes if water vapour is present, and therefore, water vapour must be removed. A gaseous mixture, or a liquefied gaseous mixture, comprising $CO_2$, water and possibly other components, could have its water content reduced by passing the mixture through a bed of switchable desiccants: water and some $CO_2$ would become bound to the switchable desiccants, and thereby be stripped out of the mixture. The switchable desiccants could then be regenerated by application of heat and/or a non-acidic gas or gas mixture such as air, dry air, or nitrogen.

Example 4: Deposition of an Amino-Alcohol on a Silicon Oxide Wafer

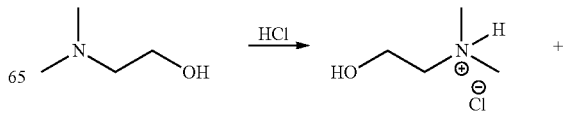

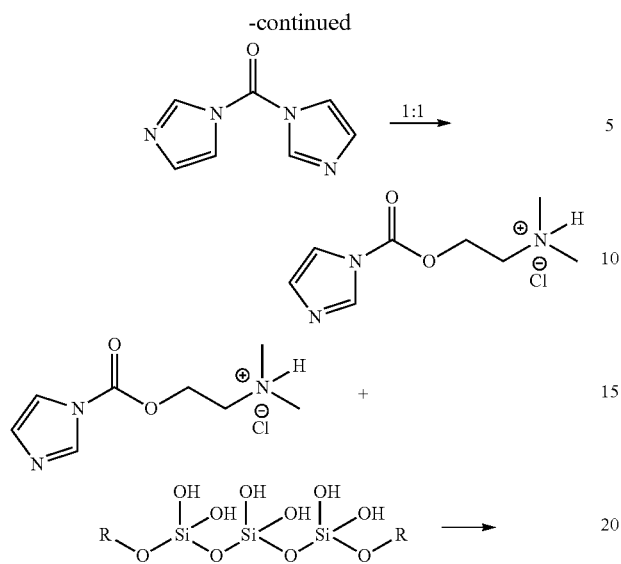
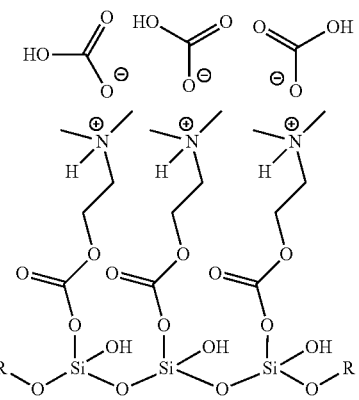
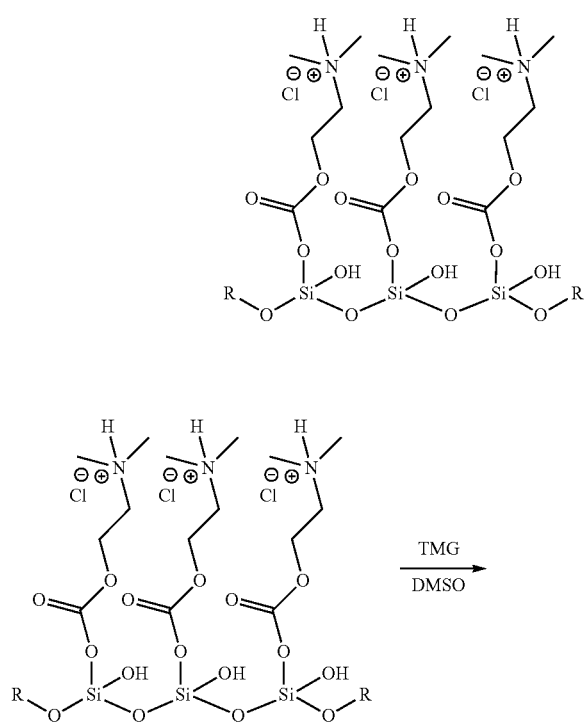
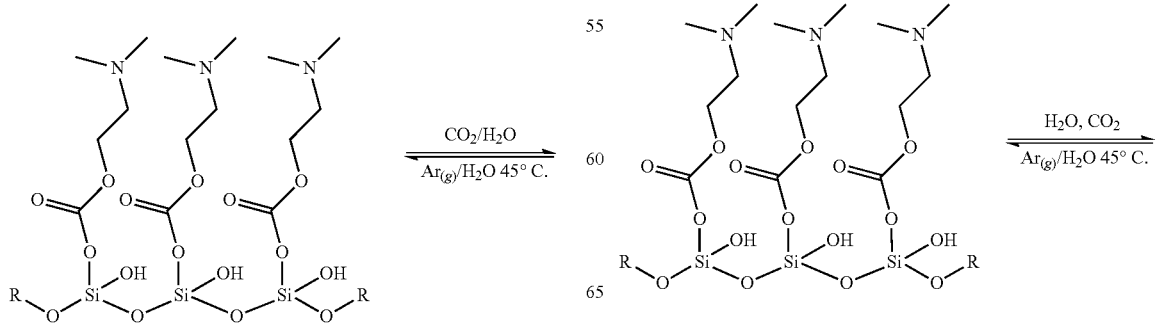

Figure 12:
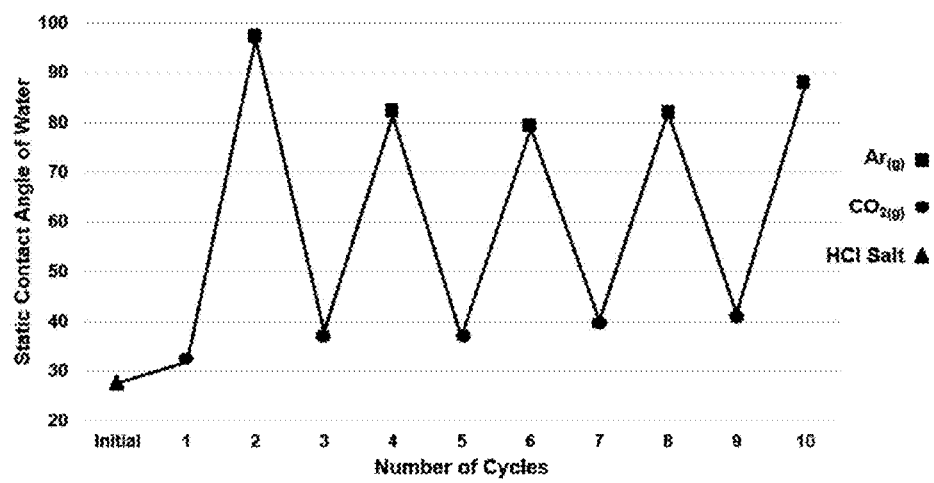
FIG. 12 depicts an 2-dimethylaminoethanol-functionalized silicon wafer's switchability between a hydrophobic and hydrophilic state upon exposure to $CO_2$ and then Ar.

2-Dimethylaminoethanol was distilled under vacuum, and dissolved in a minimum amount of ethyl acetate (1 eq. (0.5396 g, 2.50 mmol) in 30 mL). To this solution, 0.8 eq. of 38% hydrochloric acid (10.42 M) was added drop wise. A resulting aqueous layer was separated and the water removed under vacuum. An isolated hydrochloride salt of 2-dimethylaminoethanol was added to a solution of 1.0 eq. carbonyldiimidazole (0.42 g, 2.50 mmol) in a minimum of N,N-Dimethylacetamide (saturated solution). This mixture was allowed to react for 24 hours, after which it was added to a vial containing a cleaned silicon oxide wafer. This mixture sat at room temperature for 48 hours, after which a then functionalized wafer was rinsed with a solution of dimethylsulfoxide (40 mL) and 1,1,3,3-tetramethylguanidine (10 mL). The wafer was then rinsed in distilled water, dried under a stream of $Ar_{(g)}$ and subjected to switchability testing (see FIG. 12).

It was observed that the foregoing reaction was more successful (i.e. surface functionalization occurred) when non-anhydrous solvents were used. Without wishing to be bound by theory, it was postulated that water present in the solvent was protonating the imidazole group, making it a better leaving group, facilitating the reaction overall. Work is currently underway to establish whether a controlled addition of water or controlled addition of a non-nucelophilic base can catalyze the surface functionalization reaction.

Example 4A: Switchablility Testing of Amino-Functionalized Silicon Oxide Wafer

-continued

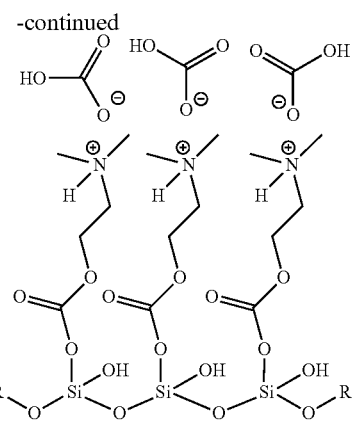

Figure 13:
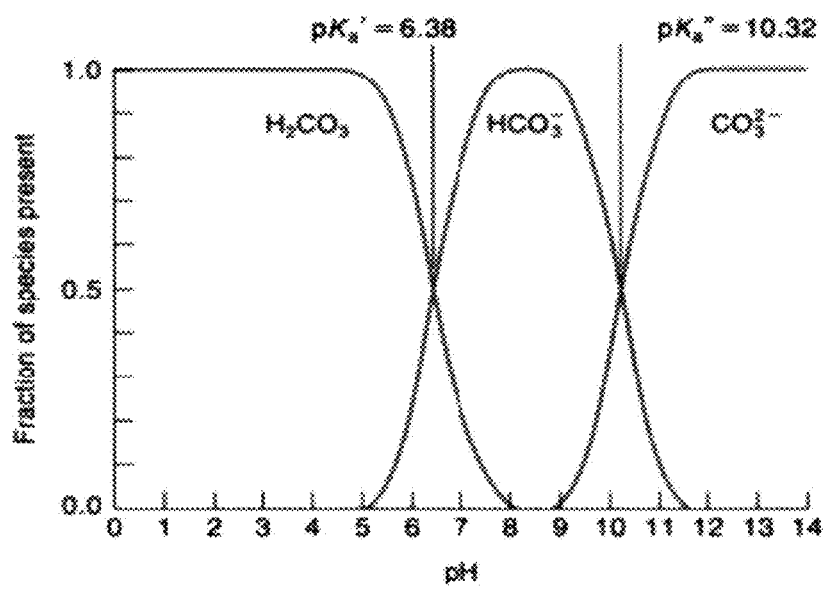
FIG. 13 depicts a species distribution related to carbonic acid as a function of solution pH; "$H_2CO_3$" includes both carbonic acid and hydrated $CO_2$ in solution. [Room temperature wet chemical process. http://specmat.com/room%20temperature%20wet%20chemical%20growth%20specmat.html (accessed May 2013)]

A standardized method was as follows:

A. $CO_2$ was bubbled through a gas dispersion tube into a beaker of Millipore™ water (pH 8.2) until the water's pH reached ≤5 (see FIG. 13);

B. An amino-functionalized surface (see Example 4) was placed into the $CO_2$ sparged solution for a total of 30 min. $CO_2$ was continually bubbled through the gas dispersion tube over the course of the 30 min;

C. After 30 min, it was assumed the surface had switched to become hydrophilic, and was characterized by contact angle goniometry;

D. After goniometric analysis, $Ar_{(g)}$ was sparged through a beaker of Millipore™ water, which was heated to 60° C.;

E. The functionalized surface was placed into the heated $Ar_{(g)}$ sparged solution for a total of 30 min. The solution was continually sparged with $Ar_{(g)}$ over the course of the 30 min; and F. After 30 min, it was assumed the surface had switched to become hydrophobic, and was characterized by contact angle goniometry.

Standard method for measuring a contact angle:

A surface's hydrophilicity or hydrophobicity can be measured by a quantitative analysis of a surface's surface tension. A contact angle is the angle at which a liquid interface meets a solid surface, which can be measured via contact angle goniometry. To measure an amino-functionalized wafer's contact angle, as described above, the wafer was placed onto a Goniometer's observation deck. The Goniometer then deposited a 0.75 uL droplet of Millipore™ water onto the wafer's surface, and captured a high resolution image of the droplet. Using the Goniometer's software, a contact angle can be calculated. This procedure is commonly referred to as a sessile droplet method. When one of the amino-functionalized surfaces, as described above, had been switched it a hydrophilic state, carbonated water was used instead of Millipore™ water.

The Goniometer used for measuring contact angles was not equipped to accurately measure roll-off angles of the foregoing switchable surface; roll-off angles are used to describe super-hydrophobic surface, wherein a lower angle is indicative of a more super-hydrophobic surface [*Chem. Soc. Rev.*, 2014, 43, 2784].

Figure 16:
FIG. 16 depicts water streaming off an amino-functionalized silicon wafer, qualitatively indicating its hydrophobicity.
Figure 17:
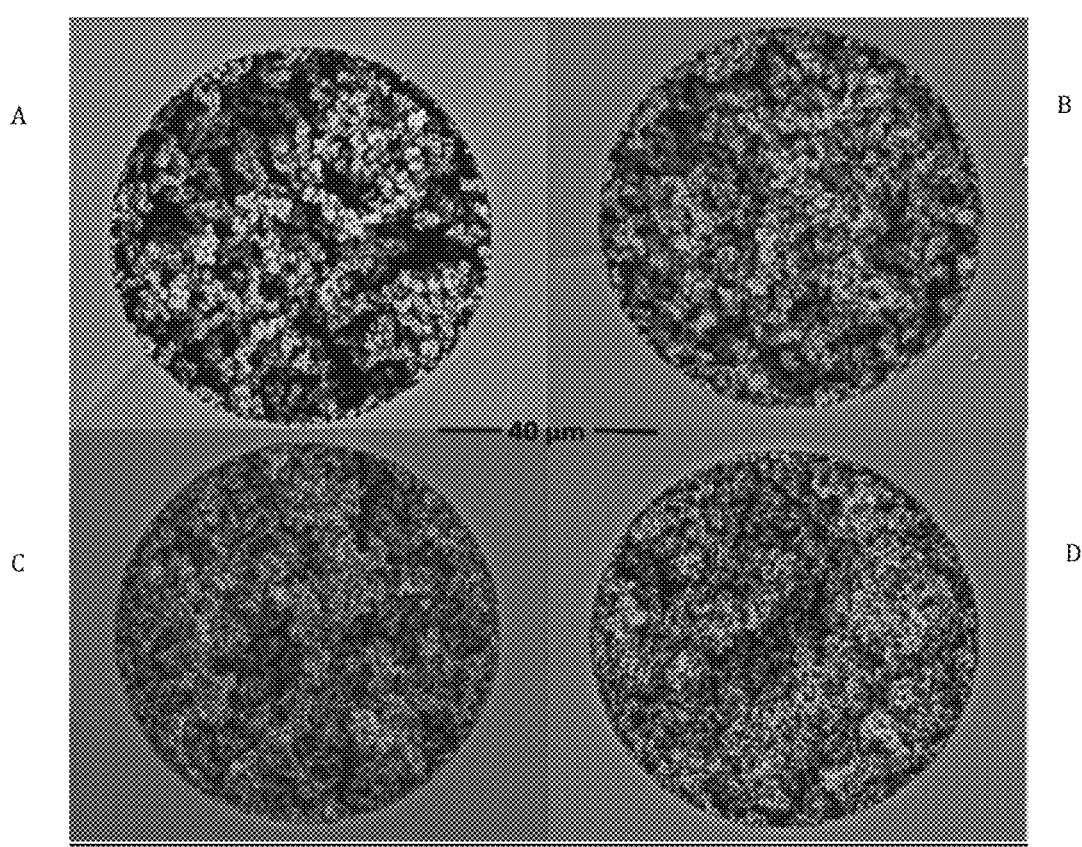
FIG. 17 depicts 3000× magnification scanning electron microscope (SEM) images of porous polymer monoliths produced with different solvent compositions (10% $H_2O$; increasing percentage of 1-propanol and decreasing 1,4-butanediol: a) 60% 1-propanol/30% 1,4-butanediol; b) 62% 1-propanol/28% 1,4-butanediol; c) 64% 1-propanol/26% 1,4-butanediol; d) 66% 1-propanol/24% 1,4-butanediol)
Figure 18:
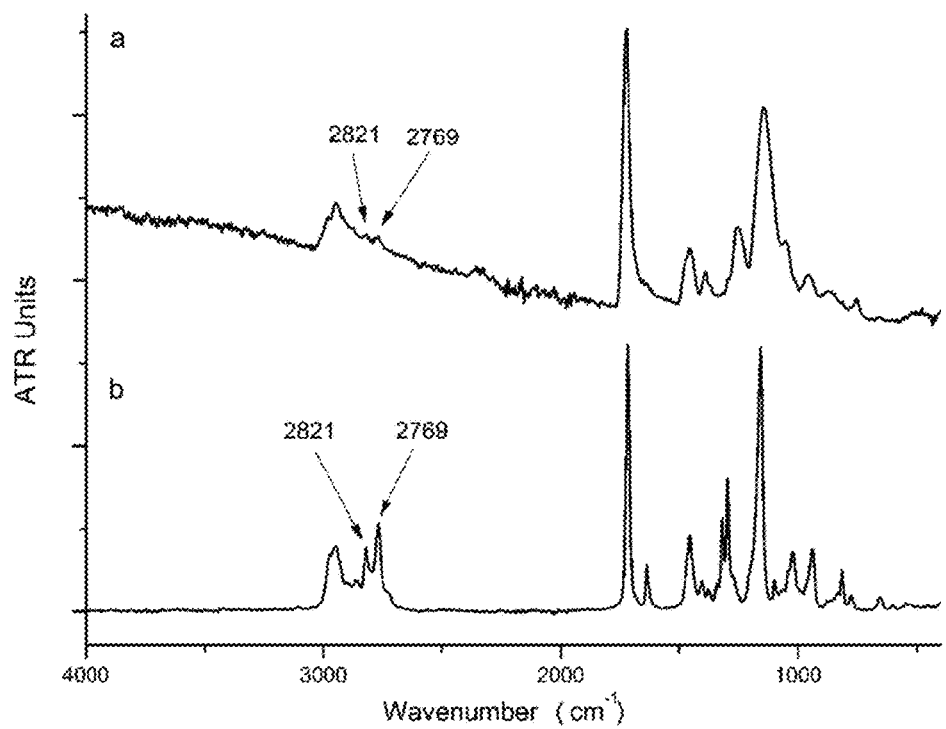
FIG. 18 depicts ATR-FTIR spectra of dimethylaminoethyl methacrylate (a) and synthesized poly(DMAEMA-co-EGDMA) porous polymer monolith (b); the polymer's IR spectrum exhibited an absorbance for tertiary amine groups from exposed DMAEMA.

As a qualitative measurement of the switchable surfaces' hydrophobicity, water was directly and continuously applied to the amino-functionalized wafer, and the water's behaviour was observed (see FIG. 16). The water readily beaded and streamed off the wafer, even at nearly level orientations (e.g. surface was parallel to floor), qualitatively indicating that the surfaces were hydrophobic.

The foregoing amino-functionalized surfaces were developed following initial investigations into silyl ether-functionalized silicon surfaces, and tertiary amine-terminated, thiol-functionalized Au surfaces (discussed below in Examples 7-7C). The silyl ether surfaces provided insight into what degrees of hydrophobicity could be imparted to a surface by varying a switchable moiety's alkane groups, allowing large property differences between a surface's hydrophobic and hydrophilic states to be obtained (herein referred to as 'magnitude of switching'); however, these systems could not be cycled multiple times, and it was postulated that the silyl ether-functionalized surfaces became stuck in a perpetual hydrophobic state. The thiol-functionalized Au surfaces (Au-thiol self-assembled monolayers, SAMs) were able to cycle three times before requiring prohibitively high energy requirements to facilitate switching between hydrophobic and hydrophilic states. This system was further limited by a lack of commercially available tertiary amine-terminated thiols to utilize, which are otherwise synthetically challenging to acquire.

In contrast, the amino-functionalized surfaces were found to exhibit a robustness that was not observed for the silyl ether-functionalized surfaces or the Au-thiol SAMs, allowing for multiple cycles between the surfaces' hydrophobic and hydrophilic states to occur (see FIG. 12); and, they were found to exhibit a large magnitude of switching, similar to that offered by the silyl-ether systems. Further, the synthetic route to amino-functionalized surfaces via CDI may offer a means through which a variety of nucleophiles containing switchable moieties could be linked to a surface.

Without wishing to be bound by theory, it is expected that surfaces functionalized with other 3° amino-alcohols would behave similarly to surfaces functionalized with the 3° amino-alcohol N,N-dimethylaminoethanol. As such, some alternatives to N,N-dimethylaminoethanol include, but are not limited to:

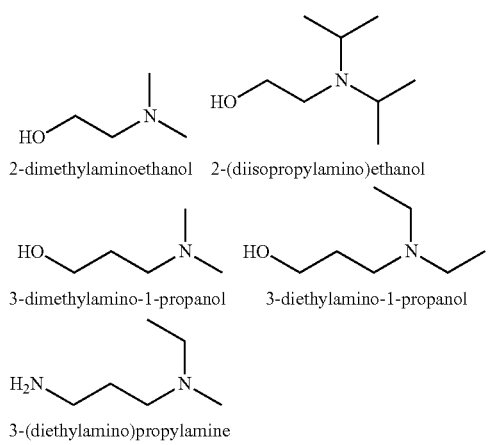

2-dimethylaminoethanol    2-(diisopropylamino)ethanol 3-dimethylamino-1-propanol    3-diethylamino-1-propanol 3-(diethylamino)propylamine Further, it has been observed that a 3-carbon linker has good thermal stability [Gelest Coupling Guide; http://www.gelest.com/gelest/forms/GeneralPages/Applications/coupling agents composites.aspx; accessed September 2014], and that 3° amines bearing at least two ethyl groups impart good switchability to a system in the presence of $CO_2$ and other benign triggers (see Table 3). As such, without wishing to be bound by theory, it is expect that N-ethylated amino-alcohols comprising a three-carbon chain to bind with a surface will produce switchable surfaces with properties such as increased thermal stability and increased hydrophobicity/hydrophilicity.

Example 5: Switchable Surfaces on Silicon Wafers Via Surface Initiated Atom Transfer Radical Polymerization (SI-ATRP)

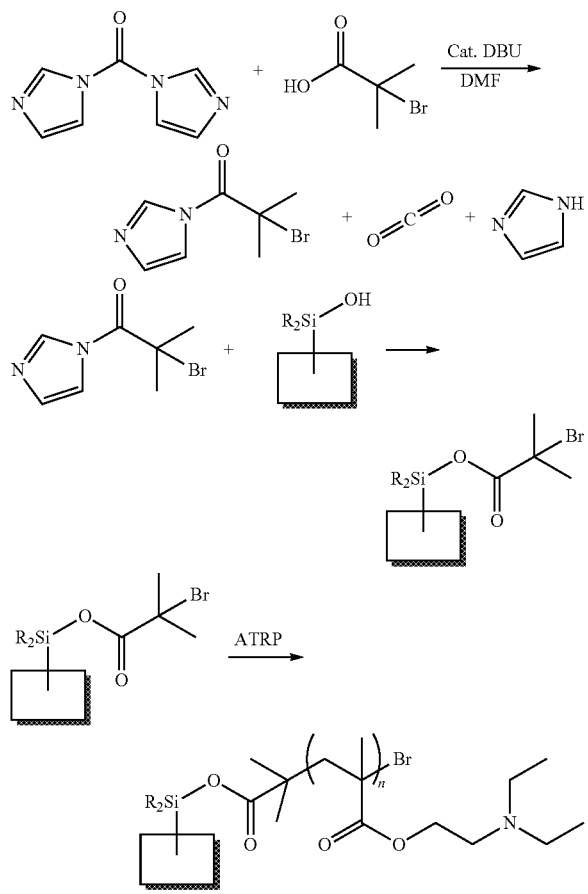

SI-ATRP is being investigated as a means of producing switchable surfaces as it a highly versatile method, for which a multitude of monomers could be employed, to a) form a $CO_2$ switchable polymer brush, or b) form a polymer brush that could be functionalized post polymerization to yield a $CO_2$ switchable polymer brush. Monomers that could be used to directly form a $CO_2$ switchable polymer brush include, but are not limited to N,N-dimethylaminoethyl methacrylate, N,N-diethylaminoethyl methacrylate, and N,N-dimethyaminopropyl methacylamide. Further, SI-ATRP offers advantages such as, but not limited to, being able to put an ATRP initiator directly on a surface, by surface functionalization, thereby allowing a controlled synthesis of polymer brushes that may exhibit a low polydispersity and a relatively uniform surface.

Si-ATRP does require a sufficient initiator concentration for the reaction to be properly controlled. As surface functionalization typically results in a low initiator concentration in the system, as compared to ATRP conducted in bulk polymerization or solution polymerization, because the number of possible sites available for functionalization on a surface is very small, the proposed SI-ATRP synthesis may not follow a traditional ATRP mechanism. One means of addressing this may be by adding sacrificial initiator to the system during the polymerization.

SI-ATRP is known in the literature of those skilled in the art [Zhao et al. Chem. Commun. 2013, 49, 90-92]. Zhao et al. reported $CO_2$-switchable polymeric brushes attached to a silicon wafer that could change water's contact angle by undergoing a morphological change, a phenomenon that they used for controlling protein adsorption. The authors used a silane-based linker, which was functionalized with a bromine-containing moiety. This combined "silane-initiator" complex was then either used as is to functionalize a surface, or it was doped with a non-initiator containing silane that competed for surface silanols during surface functionalization. Zhao et al. reported that increasing concentrations of the non-initiator-containing silane generated a system within which the initiator-containing silane was at low concentrations; this resulted in a low-density surface. Low-density surfaces result in a net reduction of steric repulsions and intermolecular interactions that can occur between neighbouring polymer brushes. Since changes in surface property resulting from use of polymer brushes are generally a consequence of morphological changes, a low-density surface would be expected to contributed to the ease at which this morphological change can occur. Zhao et al., however, do not specifically outline the exact ratios required to produce low-density surfaces within their described system.

The herein proposed work, a non-limiting example of which is outlined in the scheme of Example 5, will produce a polymer brush that is structurally distinct from Zhao et al.'s, that possesses a —$SR_2$-linker to a surface as opposed to a —$O_3Si$-linker, and that triggers changes in surface properties based off of changes in surface chemistry (see Example 5A).

Example 5A: SI-ATRP Proof-of-Concept Investigation on Silica Particles (See FIG. 21)

Silica (5 g, 40-65 uM) was added to a 50 mL round bottom flask containing 75 mL of acetone (Sigma-Aldrich, ACS reagent) and 1.22 g of potassium carbonate (Sigma-Aldrich). To this solution 2-bromo-2-methylpropionyl bromide (18 mmol, 2.22 mL, Sigma-Aldrich) was added dropwise. This solution was heated at reflux (60-65° C.) overnight. The then functionalized silica was decanted from the solution and washed multiple times with distilled water, followed by 3 washings with acetone. The particles had a distinct brown colour, and were vacuum filtered and rinsed with methanol until only white/off-white silica particles remained; excess 2-bromo-2-methylpropionyl bromide was also removed. The particles were heated in an oven at 120° C. for 20 minutes. Recovered mass of silica particles was 5.842 g.

The 2-bromo-2-methylpropionyl bromide-functionalized silica particles (2.5162 g) were used for ATRP. Dimethylaminopropyl methacylamide (DMAPMA, 17 mL, 94 mmol, Sigma-Aldrich), Cu(I)Br (1.33 g, 9.27 mmol, Sigma-Aldrich), and N,N,N',N",N"-pentamethyldiethylenetriamine (PMDETA, 3.8 mL, 18 mmol, Sigma-Aldrich) were added to methanol (40 mL, Sigma-Aldrich). The solution was then heated to 40° C. for 6 hours. The polymerized silica particles were rinsed thoroughly in methanol (three times), followed by vacuum filtration with methanol rinses. The resultant particles were used for gaseous, wet $CO_2$ capture.

General Process for Wet $CO_2$ Capture:

$CO_2$ was bubbled through a 250 mL round bottom flask containing 150 mL of water at 20±5 mL/min at room temperature. The wet $CO_2$ was then passed through a syringe containing tertiary amine-functionalized silica particles, wherein the wet $CO_2$ gas stream contained ~5% water vapour. The syringe was disconnected from the gas line at certain time intervals in order to measure the mass change. The mass was measured with an analytical balance. Residence time was 2 mL/20 ml/min=0.1 min=6 seconds. The foregoing poly-DMAPMA functionalized silica and commercially available 3-diethylaminopropyl-funcationalized silica particles were tested following this procedure (see FIG. 20).

For both trials, the particles were not fully saturated, and without wishing to be bound by theory, it is expected that if the particles had had a long period of time to interact with the wet $CO_2$, the general trend observed in FIG. 20 would continued until it plateaued.

Example 5B: Synthesis of a 2+ Component Switchable Surface (See FIG. 22)

Synthesis of a 2+ component switchable surface system is envisioned to allow for a facile attachment of various functionalities. If CDI is used effectively with silicon-based systems, essentially any nucleophilic entity can be linked to a surface via CDI. Some general approaches for acquiring such systems include: a) thiolene click reactions involving sulfur terminated silanols and polymerizable monomers (e.g. methacrylates); b) radical polymerization involving alkene terminated surfaces and polymerizable monomers; c) ATRP with monomers DEAEMA (diethylaminoethylmethacrylate), DEAPMA (diethylaminopropylmethacryamide), DMAPMA (dimethylaminopropylmethacryamide); and/or d) CDI based substitution of ATRP initiators and polymerizable monomers.

Thiolene click reactions offer a facile method of connecting a surface-linking group to a $CO_2$ switchable functionality. With this approach, either a surface-linking group needs to terminate with a thiol group, a connecting molecule needs to terminate with a thiol group, or a $CO_2$ switchable functionality needs to comprise a thiol group, somewhere on the molecule. Sulfur and nitrogen share similar reactivities, however, and often compete as nucleophiles; as such, options for molecules containing both a $CO_2$ switchable and thiol functionality are limited. As such, one approach involves either using a thiol-terminated surface, or using a thiol functionality as a connecting molecule.

For example:
a. A surface bound molecule with a thiol (see FIG. 23), wherein other known methacrylate monomers could be used, or new monomers could be synthesized via a nucleophilic substitution with methacryloyl chloride and an amino alcohol or diamine;
b. A thiol based molecule used as a connecting group, wherein a silicon surface could be coated with 3-(trimethoxysilyl)propyl methacrylate via a thiolene reaction with 1-tioglycerol, after which an alcohol terminated surface could be treated with carbonyldiimidiazole and an amino alcohol or a diamine, resulting in a $CO_2$ switchable surface (see FIG. 24);

Alternatively, a system could be developed involving amide instead ester linkages. It is known by those skilled in the art that amide linkages are generally more hydrolytically stable that ester linkages, and thus, a switchable surface comprising amide linkages may be more robust than systems comprising ester linkages.

See FIG. 25 for an example.

Example 6: Super-Hydrophobic and Super-Hydrophilic Surfaces Via Functionalized-Roughed Surfaces (See FIG. 26)

It has been demonstrated in the literature that a roughened surface is a necessary component for creating super-hydrophobic materials [Langmuir 2011, 27, 5927-5935]. Consequently, without wishing to be bound by theory, it has been considered that a surface's switchable properties may be enhanced if the surface is roughened before being functionalized: that a roughened surface functionalized with a switchable moiety may be able to switch between a super-hydrophobic state and a super-hydrophilic state. General procedure to roughen a silicon wafer surface for functionalization:

Silicon wafers (1 cm by 1 cm) were subjected to the following treatments:
a) treated in acidic piranha solution (7:3 $H_2SO_4$: 30% $H_2O_2$) for 1 h
b) treated in basic piranha solution (5:1:1 Water: $NH_4OH$: 30% $H_2O_2$) for 20 min
c) treated in HF for 1 min
d) the wafers were then rinsed in distilled water and dried under a stream of $Ar_{(g)}$.

Figure 14:
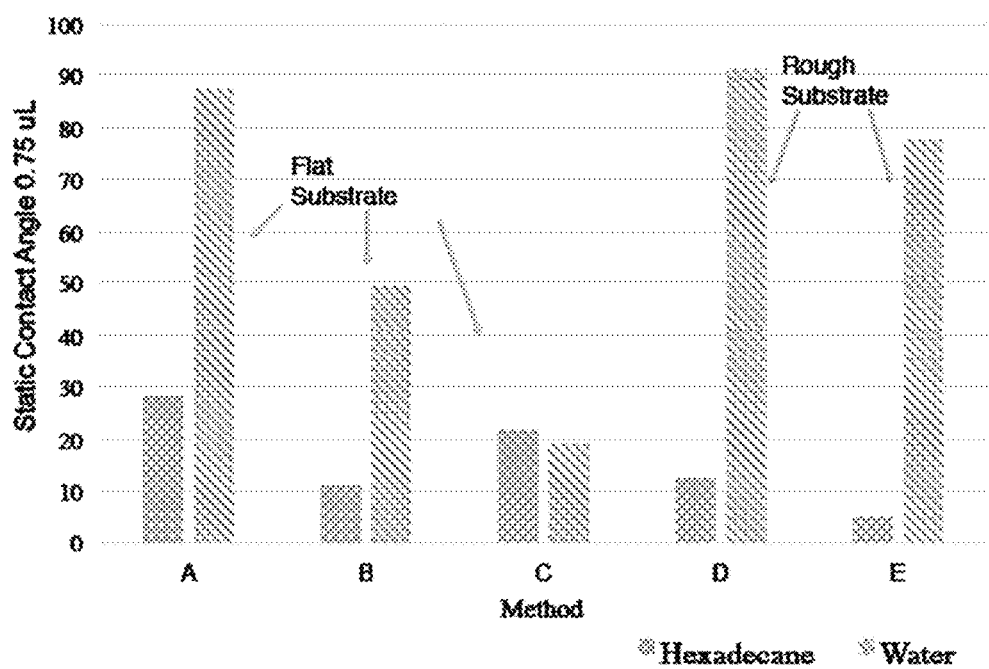
FIG. 14 depicts static contact angles of flat and roughened silicon wafer surfaces, as dependent on treatment/cleaning method.

Proof of concept for enhancing hydrophobicity by roughening a surface (see FIG. 14):
A: Control silicon wafer, used as received from manufacturer
B: Silicon wafer treated with acidic piranha solution (7:3 $H_2SO_4$: 30% $H_2O_2$)
C: Silicon wafer treated with acidic piranha solution (7:3 $H_2SO_4$: 30% $H_2O_2$), followed by treatment with basic piranha solution (5:1:1 Water: $NH_4OH$: 30% $H_2O_2$)
D: Silicon wafer treated with acidic piranha solution (7:3 $H_2SO_4$: 30% $H_2O_2$), followed by treatment with basic piranha solution (5:1:1 Water: $NH_4OH$: 30% $H_2O_2$) and treatment with HF (known etchant of silicon)
E: Silicon wafer treated with HF Following treatment with piranha solutions and/or HF, each surface was analysed goniometrically to measure its hydrophobicity. It was found that surfaces B-C were not 'roughened' by their treatment with acidic and/or basic piranha solution, while surfaces D-E were roughened by their treatment with HF, as evidenced by the observed contact angles; water's behaviour on a surface (e.g. contact angle) is indicative of a surface's texture (e.g. rough vs. smooth). Following the method outlined above for measuring a surfaces contact angle, hexadecane and water contact angles were measured for each surface (see above and FIG. 14). The high water contact angles observed for surfaces D and E suggest that roughening a surface can enhance that surface's hydrophobicity.

The aforementioned procedures for producing a switchable material on a flat/smooth surface will be applied to a roughened surface. As explained above, it is expected that a roughened surface will increase the magnitude of the surface's switch between its hydrophobic and hydrophilic states. Such an increase in magnitude may increase a switchable material's academic, commercial, and/or industrial applicability.

Example 7: Pre-Treatment of Surfaces to be Functionalized with Switchable Moieties Surfaces to be functionalized included test grade silicon wafers [N-type, phosphorous-doped, with an orientation of (100), from universitywafer.com]; glass microscope slides (from Fisher Scientific), and epitaxial gold on mica [size 75×25 mm², with (111)-layer of gold, 300 nm thickness, from George Albert physical vapour deposition coatings, (Germany)]. Pre-treatment of silicon wafers and/or glass microscope slides was performed as follows:
1. Wafers/slides were cut into 1 cm by 1 cm pieces for XPS analysis, or 2 cm×2 cm for contact angle analysis only.
2. Cut pieces were submersed in piranha solution at 85° C., for 1 h. Piranha solution consists of a 7:3 mixture of concentrated sulfuric acid to Perdrogen™ (Sigma Aldrich, 30% Hydrogen peroxide solution).
3. Wafers/slides were rinsed excessively with deionized water (50 mL), and blown dry under a stream of Ar for approximately 4 min per wafer.
4. A 5:1:1 v/v/v mixture of $H_2O$: 30% $H_2O_2$: $NH_4OH$ was prepared. This mixture was heated to 70° C. and the wafers were exposed to the mixture for 20 min: wafers were added to the mixture with gentle stirring.
5. Wafers/slides were rinsed excessively with deionized water, and blown dry with Ar.
6. Wafers/slides were either functionalized immediately or stored for future use. Wafers/slides were stored separately in clean, dry petri dishes. The petri dishes were backfilled with argon and sealed with parafilm. The sealed petri dishes were stored in a desiccator to minimize contact with atmospheric moisture, and oxygen.

Pre-treatment of gold on mica was performed as follows:
1. 1 cm by 1 cm squares were cut with a diamond tip hand held cutter.
2. Each square was rinsed with acetone (50 mL) and blown dry under a stream of Ar for approximately 4 min per square.
3. Clean, dry, squares were then functionalized immediately.

Example 7A: Functionalization of Glass Slides with Switchable Polymer Thin-Films to Form Switchable Surface Thin films of 50,000 molecular weight (Mw) poly(diethylamino)ethylmethacrylate (PDEAEMA) polymers and copolymers (FIG. 9) were prepared by radical polymerization and spun onto pre-treated glass microscope slides as follows:
1. Polymer solutions were prepared to yield concentrations of 2 mg/mL in methanol (FIG. 9, structures 5 and 6) or tetrahydrofuran (FIG. 9, structure 7).
2. Polymer solutions were spin-coated onto clean glass microscope slides at 5,000 RPM.
3. Coated slides were oven cured at 110° C. for 5-10 min.

Example 7B: Testing Switchability of Glass Slide Supported Switchable Polymer Thin-Films Thin films of PDEAEMA polymers (FIG. 9), spun onto cleaned glass microscope slides, were tested for switchability as follows:
1. Carbon dioxide (3.0 purity, Praxair) was bubbled through a gas dispersion tube into a beaker of Millipore™ water (pH 8.2) until pH was <4.
2. Glass-slide supported PDEAEMA thin films were placed into the low pH solution for a total of 30 min. $CO_2$ was continually bubbled through the gas dispersion tube for those 30 min.
3. After 30 min., it was expected that the PDEAEMA thin films had been converted to their hydrophilic form, which was subsequently characterized by contact angle goniometry.
4. Procedure to measure contact angle goniometry was as follows: a slide was positioned in front of a camera; a computer was used to deposit a drop of water onto the slide; image was captured and then measured using computer software. NOTE: If a hydrophilic form was being tested, carbonated water instead of pure water.
5. Ar was then sparged through a beaker of Millipore™ water, which was then heated to 60° C.
6. The hydrophilic forms of the PDEAEMA thin films were placed into the Millipore™ water for a total of 30 min. This mixture was continually sparged with Ar for those 30 min.
7. After 30 min, it was expected that the PDEAEMA thin films had been converted to their hydrophobic form, which was subsequently characterized by contact angle goniometry, as described above.

Figure 9:
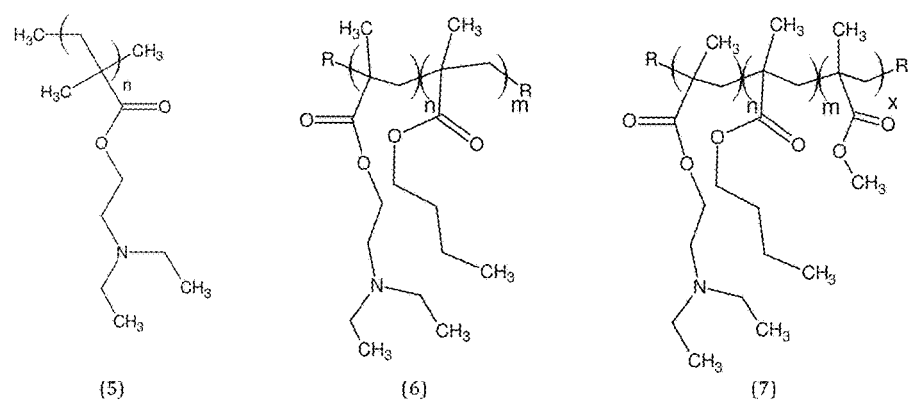
FIG. 9 depicts poly(2-diethylaminoethyl methacrylate) (PDEAEMA), and PDEAEMA co-polymers.

Initial characterization of the PDEAEMA thin films proved difficult; PDEAEMA (an amorphous polymer; FIG. 9, structure 5) has a low glass transition temperature ($T_g=16°$ C.) Below its $T_g$, a polymer will be glassy, hard and brittle. Above its $T_g$, a polymer will be in a molten or rubbery state, making it difficult to manipulate and weigh precisely. Once the PDEAEMA thin film was exposed to $CO_2$ in water, the polymer film separated from its glass slide, and partially dissolved in solution. This presented two challenges: (1) the polymer's high solubility in water and (2) its low $T_g$. In some embodiments, a $T_g$ higher than room temperature, and a lower solubility in water were used.

Figure 11:
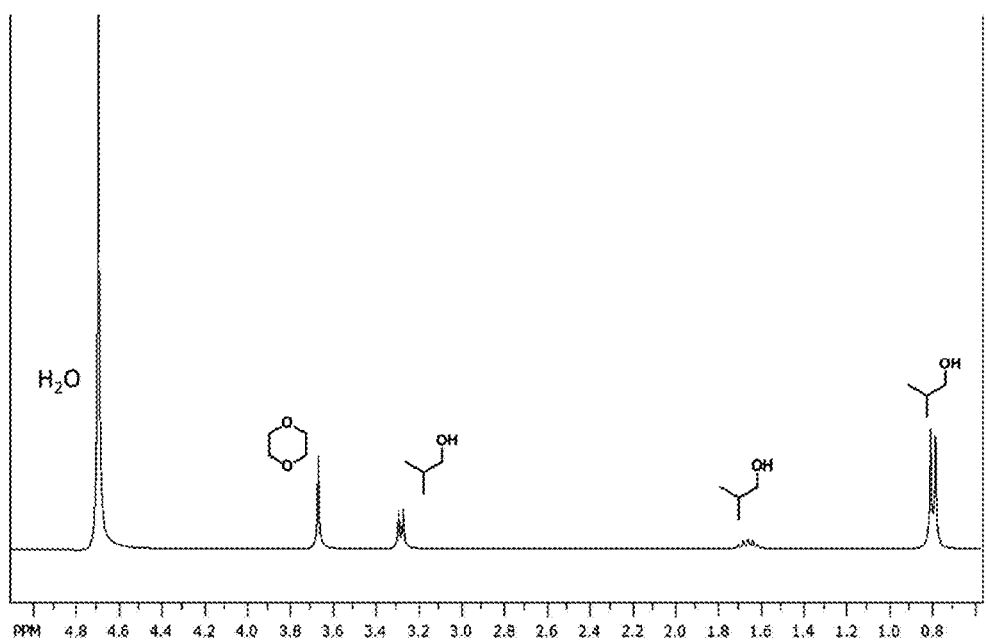
FIG. 11 depicts a $^1H$ NMR spectrum showing residual isobutanol and internal standard (1,4-dioxane) present in $D_2O$ after an acidic extraction from cross-linked polymer beads.

In order to decrease PDEAEMA's water solubility, a water insoluble monomer was added. Butyl methacrylate (Bu-MA) has a water solubility of 3 g/L, which is approximately 16 times less soluble in water than N,N-dimethylaminoethyl methacrylate (DMAEMA) [BASF, petrochemicals specialty monomers; www.spezialmonomere.basf.com/portal/load/fid235729/TI_DMAEMA.pdf]. Butyl methacrylate was copolymerized with DEAEMA at varying ratios in order to lower water solubility of the resultant co-polymer (FIG. 11, structure 6). This approach addressed the water solubility issue; however, the co-polymer had a $T_g$ of approximately 17° C., and was difficult to work with due to high viscosity. Unfortunately, the DEAEMA and Bu-MA copolymer also separated from its glass slide when attempting to switch the copolymer between its hydrophobic and hydrophilic forms.

Poly(methyl methacrylate) has a $T_g$ of 104° C. [Wittmann, J. C.; et al., *J. Polym. Sci. C.* 1969, 16, 4443]; as such, it was considered a suitable candidate to raise a copolymer's overall $T_g$. DEAEMA, Bu-MA, and methyl methacrylate (MMA) were co-polymerized at a 1:1:1 molar ratio to yield a terpolymer with an adequate $T_g$ (45° C.) and a sufficiently low water solubility. Unfortunately, the resultant terpolymer still had issues with remaining attached to the glass slide. Generation of the terpolymer's hydrophilic form, an ammonium hydrogen carbonate species, raised the terpolymer's water solubility such that it peeled off the slide.

It was thus concluded that polymer-thin films were not a readily viable means for accessing a switchable surface with academically, industrially, and/or commercially desirable properties, such as, but not limited to: physical and chemical stability and repeatable switchability under desired conditions of use. Without wishing to be bound by theory, however, it was considered that one embodiment of the foregoing may include: a) having solid surfaces or solid objects made of a polymer comprising switchable moieties, such as, but not limited to amidines or amines or b) having a thin film or coating of switchable plastic on the surface of an object, wherein the thin film or coating is attached to the object in such a way that unwanted peeling does not readily occur.

Example 7C: Deposition of a Switchable Silane Moiety on a Silicon Wafer or Glass Slide Functionalization of a silicon wafer or glass slide was performed as follows:
1. 50 mL of a 95:5 v/v ethanol and water solution was prepared.
2. The solution was adjusted to a pH of approximately 12 using either triethylamine or ammonium hydroxide.
3. Switchable silane compound (0.4-1.2 mL silane) of choice was added to the basic solution (20-60 mL) with magnetic stirring, to yield a 2% final concentration (Table 3).
4. Silicon wafers or glass slides were then added to the basic silane solution, and completely submerged in solution for 1 h, with or without stirring.
5. The wafers/slides were then removed and rinsed with ethanol (50 mL).
6. Rinsed wafers/slides were then sonicated in ethanol for 10-15 min. This was repeated twice, with fresh anhydrous ethanol (~25 mL) each time.
7. Functionalized wafers/slides were then blown dry under a stream of Ar for approximately 4 min, and were left in a fumehood for 24 h to cure at room temperature.
8. Functionalized wafers/slides were stored via the method for storing pre-treated surfaces, or were tested immediately.

In the present example, the problems associated the materials prepared by coating a surface with a switchable film (i.e., desorption of the film), were addressed by functionalizing a surface of a solid material by covalent attachment of a switchable moiety. As such, direct functionalization of a silicon wafer or glass slide was tested using silanes bearing a switchable moiety. Results are summarized in Table 3. To produce high quality, properly functionalized surfaces, pre-treated surfaces were often functionalized immediately after the pre-treatment process. This minimized unwanted surface oxidation and contamination.

A control, hexyltrimethoxysilane, was used to functionalize the silicon or glass surfaces to establish whether direct bond formation between the surface and silane would be strong enough to withstand $CO_2$ switching processes. Hexyltrimethoxysilane was chosen as a test compound because it was structurally similar to silanes bearing switchable functional groups (Table 3), but did not contain a switchable functional group itself. Since hexyltrimethoxysilane's hydrophobic form was consistent before and after $CO_2$ exposure (Table 3), it was concluded that a Si—O—Si bond was strong enough to withstand the switching process. As such, a variety of amine or amidine-containing silanes were tested for $CO_2$ switchability (Table 3). [3-(diethylamino)propyl]-trimethoxysilane offered the largest change in contact angle upon switching between its hydrophilic form and its hydrophobic form. Consequently, [3-(diethylamino)propyl]-trimethoxysilane was selected for further testing. This material was successfully switched from a hydrophobic form to its hydrophilic form by introducing $CO_2$. Addition of Ar or heat resulted in the switch of the material back to its hydrophobic form, but the material was not readily switched back to its hydrophilic form with the reintroduction of $CO_2$.

It was thus determined that switchable silane moieties attached to silicon surfaces via Si—O—Si linkages were not a readily viable means for accessing a switchable surface with academically, industrially, and/or commercially desirable properties, such as, but not limited to: physical and chemical stability and repeatable switchability under desired conditions of use.

Figure 10:
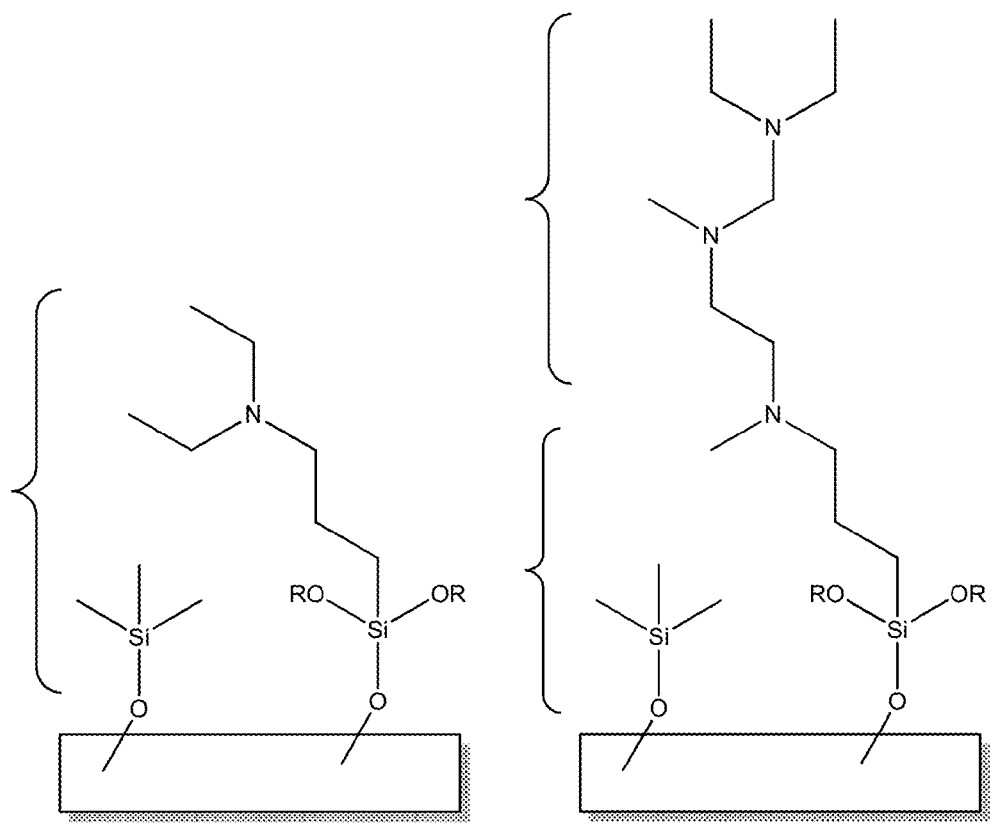
FIG. 10 depicts a surface adapted to prevent a persistent hydrophobic form of a switchable surface, indicating distinct domains that influence overall surface properties.

Without being bound by theory, it was postulated that creating a raised "effective surface" (FIG. 10) by introducing longer and/or larger monovalent or divalent moieties to the switchable moiety may put enough distance between any hydrophilic and hydrophobic surfaces to create two separate domains. Having two distinct domains may be sufficient enough to allow the surface to exhibit switchability. This could be accomplished via a thiol-ene click reaction, SI-ATRP, or by using extended alkyl chains between the surface-linking group and the switchable moiety.

A raised effective surface could be produce by first functionalizing a surface with an alkene-substituted silyl reagent such as, but not limited to, 3-(trimethoxysilyl)propyl methacrylate. Once prepared, said functionalized surface could be treated with 1,1,1,3,3,3-hexamethyldisilazane+trimethylchlorosilane (HMDS-TMCS) to functionalize any surface silanols that remain unfunctionalized. Following treatment with HMDS-TMCS, a thiol bearing a switchable moiety such as, but not limited to, N'-(6-mercaptohexyl)-N,N-dimethylacetimidamide, could be "clicked" following thiol-ene click literature procedures to produce a raised effective surface [Boyer, C.; Soeriyadi, A.; Roth, P.; Whittaker, M.; Davis, T. Chem. Commun. 2011, 47, 1318].

Other options of obtaining a raised effective surface include, but are not limited to, chemospecific reactions, such as the Eschweiler-Clarke reaction [Eschweiler, W. (1905), Ersatz von an Stickstoff gebundenen Wasserstoffatomen durch die Methylgruppe mit Hülfe von Formaldehyd. Ber. Dtsch. Chem. Ges., 38: 880-882; H. T. Clarke, H. B. Gillespie, and S. Z. Weisshaus Journal of the American Chemical Society 1933 55 (11), 4571-4587]. This reaction constitutes a conversion of primary amine into a tertiary amine; as such, it would not create a raised effective surface, but could aid in a later stage transformation of a long chain primary amine (which can raise the surface) into a $CO_2$ switchable tertiary amine.

Example 7D: Formation of Amidino-Functionalized Thiol Self-Assembled Monolayers (SAM) on Gold N'-(6-Mercaptohexyl)-N,N-dimethylacetimidamide was synthesized as follows:

6-Amino-1-hexanethiol hydrochloride (Sigma Aldrich, $0.1026 \times 10^4$ mol) was mixed with Amberlite-OH exchange resin (1.02 g) and 3 Å molecular sieves (0.026 g) in methanol (40 mL), and magnetically stirred for approximately 24 h. The mixture was then filtered and any liquid components were decanted into a new round bottom flask. To the new round bottom flask, N,N-dimethylacetamide dimethyl acetal (TCI America, stabilized in 5-10% methanol, 0.68 mmol) was added and the mixture was stirred at 60° C. for 3 h. Any volatile components (methanol and by-product) were then removed under vacuum, and the crude product was treated with $NaBH_4$ (30 mg in water) at 50° C. for 30 min. Any remaining $NaBH_4$ was neutralized, and the crude product mixture was protonated with an acidic workup. Sodium chloride salts were filtered out of the mixture and the water was removed under vacuum. Isolated N'-(6-Mercaptohexyl)-N,N-dimethyl acetimidamide was purified using a short silica column and a 40:60 v/v acetonitrile to ethanol mobile phase. The purified product, N'-(6-mercaptohexyl)-N,N-dimethylacetimidamide (30 mg, 0.15 mmol, 25% yield), was characterized via $^{13}$C NMR and $^{1}$H-$^{13}$C HSQC (Heteronuclear Single Quantum Correlation) NMR spectroscopy. Appearance of a quaternary carbon at approximately 180 ppm confirmed that the amidine functionality had been synthesized and high resolution mass spectrometry confirmed an expected molecular weight of 202 g/mol.

Functionalization of a cleaned gold substrate was performed as follows:
1. Select thiol compound (25 mg) was added to anhydrous ethanol (6.5 mL) and then further diluted (3.2 mL of thiol solution into 8.8 mL anhydrous ethanol) to yield a final concentration of 1-5 mM.
2. The pH of the solution was adjusted to approximately 12 via addition of 1,1,3,3-tetramethylguanidine.
3. Gold surfaces were added to a scintillation vial, and left in solution for 48 h. The vial was backfilled with Ar and sealed with the vial's cap.
4. Functionalized gold surfaces were removed and rinsed with the pH-adjusted solution for 10-15 s. The surfaces were then rinsed thoroughly with anhydrous ethanol (50 mL), and blown dry under a stream of Ar for approximately 4 min.
5. Functionalized gold surfaces were stored via the method for pre-treated surfaces, or were analyzed immediately for contact angle via the method discussed previously.

A self-assembled monolayer (SAM)-functionalized gold surface as a switchable surface was studied as an alternative in which potential acid-base interactions between free surface silanols and switchable moieties would be eliminated. A self-assembled monolayer was created using N'-(6-mercaptohexyl)-N,N-dimethylacetimidamide (Table 4). This SAM was cycled 3 times; however, by the third cycle, a temperature increase was necessary to induce its hydrophobic form. Removal of $CO_2$ from the SAM's ammonium hydrogen carbonate form was unsuccessful at 60° C. Partial regeneration of the SAM-functionalized gold surface's hydrophobic form was observed at 70° C.; full regeneration was not observed until 80° C., which is sufficiently high to limit the energy savings offered by a switchable system (for example, see Example 4). Further, efficient use of SAMs currently requires Au surfaces, which are expensive and not practical for wide-spread use lining industrial pipelines or reaction vessels; also, tertiary amino-thiols are not readily available commercially, nor are amidino-thiols.

It was thus concluded that amidino-functionalized thiol self-assembled monolayers on gold were not a readily viable means for accessing a switchable surface with academically, industrially, and/or commercially desirable properties, such as, but not limited to: physical and chemical stability and repeatable switchability under desired conditions of use.

Example 8: Switchable Chromatagraphic Supports for Use in Solid Phase Extraction (SPE) (See FIG. 27)

SPE is a technique used to concentrate, separate, and isolate very dilute analytes from samples such as aqueous solutions (lake water, etc.) or biological specimens, wherein biomolecules as such nucleic acids require amplification.

For SPE to be most successful, it requires a stationary phase that can strongly bind dilute concentrations of a desired analyte(s) with use of one mobile phase (e.g. polar solvent), and then readily separate and release said analyte(s) with use of another mobile phase (e.g. non-polar organic solvent); or, requires use of the same mobile phase under different conditions, such that the desired analyte is released from the SPE stationary phase.

If the stationary phase for a solid phase extraction was switchable from a hydrophobic state to a hydrophilic state in the presence of $H_2O$ or $H_2O$ and $CO_2$, it would allow desired analytes to be strongly bound in the presence of one benign mobile phase (e.g. $H_2O$), and then readily separated and isolated with another benign mobile phase (e.g. $H_2O$ and $CO_2$). This would allow use of non-hazardous, non-flammable aqueous solvents, reduce need for traditional chromatographic organic solvents, reduce costs in said solvent disposal, and would provide another dimension in chromatographic control by modulating a stationary phase's polarity.

Preparation and use of a switchable SPE column (see Table 5):

Packing material: $Si(CH_2)_nN(CH_3)_2$ (1.0 g & 5.0 g), topped with glass wool or sea sand. Analyte loading: 2 mL of a 0.035 M (35-45 mg) solution of three phenols (2,6-dimethylphenol; phenol; 2-hydroxyphenol). Solvent: 100% $H_2O$ or 80% $H_2O$/MeOH.

Figure 15:
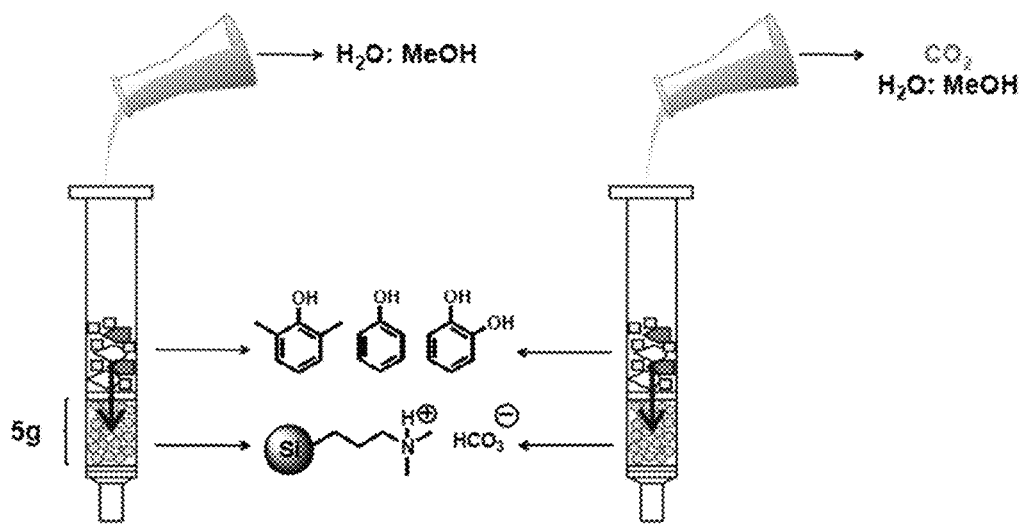
FIG. 15 depicts an embodiment of switchable chromatographic supports being used as a stationary phase in solid phase extractions.

As delineated in Table 5, trials 1, 3, and 4 used $Si(CH_2)_nN(CH_3)_2$ as a stationary phase and 80% $H_2O$/MeOH as a mobile phase; trials 2 and 5 used $Si(CH_2)_nN(CH_3)_2H^+$ and carbonated 80% $H_2O$/MeOH (see FIG. 15). Aliquots were collected from the SPE column in 30-second intervals, wherein elution time 1, 2 and 3 refers to elution of 1,2-dihydroxybenzene, phenol and 2,6-dimethylphenol respectively; isolated phenol compounds were detected by Thin Layer Chromatography (TLC). To be considered "soluble" in the mobile phase, the phenol compounds needed to be detectable by TLC.

These results, as delineated in Table 5, suggest that compounds can be separated from a mixture, and then eluted from a SPE column with shorter retention times, with use of an aqueous carbonated, or non-carbonated, mobile phase. If a compound remains strongly bound to a column due to its interaction with the column's stationary phase, it may be more readily eluted using an aqueous, carbonated mobile phase. For example, this could allow a user to elute one component of a solution or mixture off of an SPE column using an aqueous, non-carbonated mobile phase, and then subsequently elute any component remaining strongly bound to the stationary phase by use of an aqueous, carbonated mobile phase. Alternatively, if a compound is not strongly bound to a SPE column's stationary phase, the foregoing results suggest that this process could be used to reduce said compound's retention time.

Other embodiments may include use of packing materials such as, but not limited to, $Si(CH_2)nN(CH_2CH_3)_2$, and analytes such as, but not limited to, amines, carboxylic acids, esters, ketones, and aldehydes.

Example 8A: Switchable Monolith Columns for Chromatographic Applications

Preparation of a Switchable Monolith Column Via Direct Copolymer Synthesis and Epoxide Surface Functionalization Copolymer Monolith #1

Dimethylaminoethyl methacrylate (DMAEMA), ethylene glycol dimethacrylate (EGDMA), azobisisobutyronitrile (AIBN), 3-(trimethoxysilyl)propyl methacrylate (γ-MAPS), glacial aceticacid, 1-propanol, 1,4-butanediol, phenanthrene (98%), anthracene (98%) were acquired from Sigma-Aldrich, acetonitrile (HPLC grade), formic acid (98%) was purchased from BDHChemicals (Toronto, ON), water for aqueous solutions and HPLC mobile phase wasprepared from Milli-Q water purification system. 3 mL Luer-Lock Tip syringes were used (Franklin Lakes, N.J.). TSP075375 fused silica capillary tubing was purchased from Polymicro Technologies Phoenix, Ariz.). Thermogreen LB-2 Septa disks were acquired from Sigma-Aldrich LLC (St. Louis, Mo.).

Syringe pump from Harvard Apparatus was used for syringe pumping (Holliston, Mass.). Waters nanoAcquity UPLC system was fitted with a tunable UV detector, and operated by the MassLynx software package (v 4.1). NanoTight union (P-779-01) and MicroTight Fittings (F-125X; sleeve F-185X) from Upchurch Scientific (Oak Harbor, Wash.) were ordered to allow proper coupling of the PPM column with the high-pressure valve of the nanoAcquity.

All monoliths were formed in fused silica capillaries with 75 μm I.D. and 360 μm O.D. Prior to use, the capillaries' interiors were functionalized with vinyl groups to facilitate polymer attachment using a pre-treatment procedure originally described by Ngola et al. [Ngola, S. M.; Fintschenko, Y.; Choi, W. Y.; Shepodd, T. J. *Anal. Chem.* 2001, 73, 849-856]. Briefly, a piece of 20 cm long capillary was connected to a syringe filled with a solution of 3-(trimethoxysilyl)propyl methacrylate (γ-MAPS) (20%, v/v unless otherwise stated), purified water (50%) and glacial acetic acid (30%). A flow rate of 10 μL/min was set for an hour on the syringe pump and after that, the capillary was left with a flow rate of 0.2 μL/min overnight to react. Subsequently, the capillary was flushed by a mixture of acetonitrile (95%, v/v) and water (5%) for one hour cleanup. The flow rate of the syringe pump was 10 μL/min. The pretreated capillaries could then be used directly or stored until further use.

A polymerization reaction mixture was prepared by adding the following reagents together in sequence. For example, to prepare a reaction mixture with 60% 1-propanol in solvents, 2.5 mg AIBN (0.25%, w/v), 750 μL solvents (75 μL H$_2$O, 10%; 450 μL 1-propanol, 60%; 225 μL 1,4-butanediol, 30%), 250 μL monomers (200 μL ethylene glycol dimethacrylate, 80%; 50 μL N,N-Dimethylaminoethyl Methacrylate, 20%) were mixed by vortex blending. This mixture was placed into an ultrasonic cleaner for 5 min to exhaust residual bubbles and dissolved gas.

Similarly, the pretreated capillary was connected to a 3 mL syringe filled with the polymerization reaction mixture, and set to a flow rate of 10 μL/min for one hour. After introduction of the reaction mixture into the capillary, the capillary's two ends were sealed instantly by piercing the ends' tip into a Thermogreen GC septa disk to prevent spill. The filled capillary was then moved into an oven at 80° C. for 6 hours. Following formation and trimming (cutting off failed ends), monoliths were flushed with a solution of acetonitrile and purified water (95:5, v/v) using a binary solvents pumps for 30 min per cm of capillary monolith, at a flow rate of 2 μL/min, to remove any unreacted monomers or solvents. Finally, the capillary was trimmed into a 10 cm long piece for use.

A MLA Quanta 650 FEG-ESEM from FEI was used for imaging (Hillsboro, Oreg.). Small pieces (~5 mm) of capillaries were mounted on to aluminum stubs using tape such that an unobstructed view of their cross-section was possible, permitting examination of the polymer contained within. Prior to imaging, the 5 mm pieces of capillaries were coated with a thin layer of gold using a Hummer 6.2 Sputtering System (Anatech, Hayward, Calif.). Fourier transform infrared spectroscopy (FTIR) analysis of the monoliths was obtained from an ALPHA FTIR spectrometer (Bruker Corporation, Billerica, Calif.). A liquid sample of DMAEMA was dropped onto the sampler, and the spectrum was acquired as comparison from OPUS spectroscopy software. Following that, the porous polymer monolith material was spread onto the sample to acquire its FTIR spectrum.

Chromatographic characterization of a switchable porous polymer monolith in 75 μm I.D. columns was carried out with a Waters nanoAcquity UPLC system controlled by Masslynx software. A mobile phase used consisted of water and acetonitrile at a ratio of 55:45. pH-Responsive properties were investigated at a flow rate of 1 μL/min. Formic acid (0.1%) was added into the mobile phase solution to investigate the any change (switch) in retention behavior. UV detection wavelength was determined to be 254 nm. Injection volumes were 0.4 μL. Respectively, phenanthrene and anthracene were dissolved in 50% of aqueous acetonitrile solution (2 μg/mL). After sample solution preparation, they are injected into the monolithic column for chromatographic behavior analysis.

To produce the foregoing epoxide monolith #1, several experimental factors were optimized, including the polymerization time, monomeric composition, and porogenic solvent composition.

By changing the solvent composition, the polymer monolith's density can be controlled so that the monolith's permeability can satisfy an specific application's requirements. As depicted in FIG. 19, an increase in density, and a decrease of particle and pore size, was observed when the proportion of 1-propanol was changed from 60% to 66%. Because it is hard to measure the size of particles precisely, we put calipers directly onto the SEM images to get a rough idea about the particle size. Also, We measured the backpressure of the monolithic column by water nanoAcquity UPLC system, for 10 cm long column, with 50% aqueous acetonitrile and 400 nL/min flow rate. The equilibrated backpressure of the four group of monolithic columns increased from 353±2 psi up to 425±1 psi, 1216±1 psi and 2244±2 psi. By trading off between density and efficiency, we selected the third recipe (10% H$_2$O, 64% 1-propanol, 26% 1,4-butanediol) for further tests.

By introducing a monomer with tertiary amine groups, without wishing to be bound by theory, it was expected that the monomer's tertiary amine groups would be exposed at the monolith's surface, and thus could impart the monolith with a capacity to switch between hydrophobic and hydrophilic states. During the polymerization reaction, ethylene glycol dimethacrylate (EGDMA) was utilized to form the copolymer's backbone. To demonstrate effect of synthesis and tertiary amine group exposure, ATR-FTIR spectroscopy was used to qualify an existence of functional groups at the monolith's surface. The representative spectrum of the monomer, dimethylaminoethyl methacrylate (DMAEMA), was acquired as reference.

For the DMAEMA sample, a strong absorbance was observed at 2770 cm$^{-1}$ and 2820 cm$^{-1}$, corresponding to symmetric stretching vibrations of the monomer's —N(CH$_3$)$_2$ group (see FIG. 20a). For the monolith, a weak absorbance appears at 2821 cm$^{-1}$ and 2769 cm$^{-1}$, corresponding to the distinctive stretching vibration pattern of the tertiary amine group, —N(CH3)$_2$ (see FIG. 20b). This suggested a successful synthesis of a porous monolith with DMAEMA groups exposed at its surface.

The DMAEMA-co-EGDMA polymeric monolith's capacity to switch was evaluated by chromatographic tests with composition of mobile phase remained unchanged. As a proof of concept, formic acid was used as a pH alternative to CO$_2$ to test the switching behavior of the monolith. To demonstrate a stationary phase hydrophobicity switch, regardless of an analyte ionization effect, polycyclic aromatic hydrocarbon compounds were selected for use as test analytes. An isocratic mobile phase with water and acetonitrile (55:45), an ultraviolet detector wavelength of 254 nm, and a 1 μL/min flow rate was applied according to the aforementioned experimental process. To determine the monolith's change, or switch, in retention behavior by changing pH, 0.1% (v/v) of formic acid was added into the mobile phase (both water and acetonitrile).

By running the mobile phase with or without formic acid added, a change (switch) in retention time was observed. Phenanthrene had a retention time of 11.6 min (see FIG. 21a), which was shortened to 8.2 min (see FIG. 21b) when formic acid was added to the mobile phase. This change in retention time was also observed for anthracene, which exhibited a change in retention time from 10.3 min to 7.3 min.

It was concluded, therefore, that mobile phases with a lower pH can protonate tertiary amine groups anchored on a monolith's surface; and that, sparging a mobile phase with $CO_2$ would be sufficient to switch a monolith from a hydrophobic (non-protonated) state to a hydrophilic (protonated) state by forming charged carbamate or bicarbonate salts [Vanderveen, J. R.; Durelle, J.; Jessop, P. G. Green Chem. 2014, 16, 1187; Scott, L. M.; Robert, T.; Harjani, J. R.; Jessop, P. G. RSC Adv. 2012, 2, 4925]. Further, it was concluded that removal of $CO_2$ by sparging with a non-acidic gas, such as air, nitrogen, or argon, would be sufficient to switch a monolith from a hydrophilic (protonated) state to a hydrophobic (non-protonated) state.

Copolymer Monolith #2

To prepare a porous polymer monolith, 24% glycidyl methacrylate monomer (GMA) and 16% ethylene dimethacrylate (EDMA) cross-linker were mixed using 60% porogenic solvents (25% methanol and 75% cyclohexanol) in the presence of 1% AIBN (with respect to monomer) thermal initiator. A fused silica with 75 μm (id) was pretreated with 5:3:2 water: acetic acid: 3-(trimethoxysilyl)propyl methacrylate (MAPS) overnight and any unreacted chemicals were flushed with 95% acetonitrile for 30 minutes. The pretreated fused silica was filled with the polymer monomer and cross-linker mixture, and was kept at 60° C. for a minimum of 20 hours.

An epoxide monolith was formed at the end of the polymerization reaction. The epoxide monolith was washed with 250 μL of tetrahydrofuran (THF) to remove the porogenic solvents. Afterwards, the monolith was washed again with 250 μL of water to remove the THF, and 500 μL of 99.5 wt. % butyl amine was flushed at 5 μL/min with a syringe pump; the filled column was plugged and kept at 60° C. for another 8 hours. The butyl amine reaction was repeated in order to convert all epoxides to substituted amine compounds. Again, in order to convert any alcohol groups that will be formed as a result of the reduction of the epoxide, an esterification reaction was carried out by flashing the column with a mixture of 454.5 μL formic acid and 90 μL of sulfuric acid for 5-10 minutes, after which the saturated column was left at 90° C. for 15 minutes. Excess unreacted chemical solutions were removed by pumping water through the column at 1 μl/min overnight (for a minimum of 8 hours). pH of the flow through was tested with pH paper until the pH was the same as that of DI. Water.

Switchability of the amine-functionalized monolith from hydrophobic to hydrophilic states will be tested by using small organic molecules and peptides with and without $CO_2$ in water.

TABLE 1

Recycling of various drying agents to remove water from isobutanol solutions.[a]

| Drying agent | Accessible amine (mmol/g) | Size (μm) | Water removed[b] (mg/g) Cycle | | | |
|---|---|---|---|---|---|---|
| | | | 1 | 2 | 3 | 4 |
| Silica-NMe$_2$ | 1.7 | 20 | 180 | 140 | 160 | 140 |
| Mesoporous silica-NMe$_2$ | 1.5 | 300 | 120 | 160 | 100 | 100 |
| Polymer particles | 2.6 | 220 | 300 | 220 | 200 | 160 |
| Polymer particles | 2.6 | 220 | 380[c] | 520[c] | 400[c] | 400[c] |
| Molecular sieves[d] | — | 4000 | 380 | 40 | 60 | — |
| Silica[d] | — | 74-177 | 150 | 150 | 140 | 140 |
| Alumina[d] | — | 37-63 | 39 | 75 | 72 | 83 |

[a]Reaction conditions: 10 g isobutanol with water at a concentration of 5 wt %, 0.5 g drying agent added, 1 h mixing with $CO_2$ bubbling through solution then continued mixing in a sealed vial for 15 h, water content analyzed by GC-TCD. Drying agent regeneration was performed at 50° C. for 4 h.
[b]Water removed with respect to drying agent used.
[c]An increased bubbling time of 3 h and continued mixing under 1 atm of $CO_2$ (g) was employed.
[d]No $CO_2$ added.

TABLE 2

Results from drying isobutanol, doped with reduced water contents, using polymer beads

| Drying Agent | Water in Stock Solution[a] (wt %) | Residual Water (wt %) | Water Removed (wt %) |
|---|---|---|---|
| Polymer beads | 0.5 | 0.5 | 0.0 |
| Polymer beads | 1.0 | 0.8 | 0.2 |

Reaction conditions: 10 ml 'wet' isobutanol, 0.5 g drying agent added, 1 h mixing with $CO_2$ bubbling through solution then continued mixing in a sealed vial for 15 h, water content analyzed by GC-TCD.

TABLE 3

Contact angle goniometry analysis for hydrophilic and hydrophobic forms of silanes tested for $CO_2$ switchability

| Silane | Before $CO_2$ Exposure | After $CO_2$ exposure | Std. Deviation | Magnitude of Switch |
|---|---|---|---|---|
| 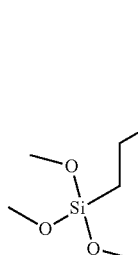 n-Hexyltrimethoxysilane | 101• | 103• | 4• | 2• |

TABLE 3-continued

Contact angle goniometry analysis for hydrophilic and hydrophobic forms of silanes tested for $CO_2$ switchability

| Silane | Before $CO_2$ Exposure | After $CO_2$ exposure | Std. Deviation | Magnitude of Switch |
|---|---|---|---|---|
| (N,N-Dimethylaminopropyl)trimethoxysilane | 87° | 57° | 6° | 30° |
| Diethylaminomethyltrimethoxysilane | 84° | 48° | 6° | 36° |
| [3-(Diethylamino)propyl]-trimethoxysilane | 94° | 20° | 9° | 74° |
| N,N-dimethyl-N'-(3-(trimethoxysilyl)propyl)acetimidamide | 69° | 42° | 9° | 27° |

TABLE 4

Contact angle goniometry results from switching a N'-(6-mercaptohexyl)-N,N-dimethylacetimidamide self-assembled monolayer on gold between its hydrophobic and hydrophilic states over 3 cycles

HS–(CH₂)₆–N=C(CH₃)–N(CH₃)₂

|  | Hydrophobic | Hydrophilic | Magnitude of Switch |
|---|---|---|---|
| Cycle 1 | 75 ± 5° | 49 ± 6° | 26° |
| Cycle 2 | 70 ± 1° | 56 ± 2° | 14° |
| Cycle 3 | 80 ± 2° | 63 ± 2° | 17° |

TABLE 5

Elution times of phenol compounds separated via SPE using a switchable chromatographic support

| Trial | Mobile Phase | Stationary Phase | Elution Time 1 | Elution Time 2 | Elution Time 3 |
|---|---|---|---|---|---|
| 1 | 80:20 H₂O:MeOH mobile phase | 1.0 g Si(CH₂)ₙNMe₂ | 2:30-12:30 | 1:30-11:00 | 1:30-11:00 |
| 2 | CO₂, 80:20 H₂O:MeOH mobile phase | 1.0 g Si(CH₂)ₙNMe₂ | 0:00-6:00 | 0:00-5:30 | 0:00-5:30 |
| 3 | 80:20 H₂O:MeOH mobile phase | 1.0 g Si(CH₂)ₙNMe₂ | 0:00-10:30 | 0:00-10.00 | 0:00-10:00 |
| 4 | 80:20 H₂O:MeOH mobile phase | 5.0 g Si(CH₂)ₙNMe₂ | 1:03:00-1:08:00 | 52:00-1:04:00 | 47:00-53:00 |
| 5 | CO₂, 80:20 H₂O:MeOH mobile phase | 5.0 g Si(CH₂)ₙNMe₂ | 45:00-50:00 | 37:00-46:00 | 26:00-38:00 |

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A composite material that is reversibly switchable between a first form and a second form, said composite material comprising a solid and solid-supported switchable moiety attached to said solid via a linker, wherein the attachment to said solid does not comprise a Si—O—Si or S—Au bond, the switchable moiety comprising a functional group that is switchable between a neutral form associated with said first form of said composite material, and an ionized form associated with said second form of the composite material, wherein the linker is not a polyamine, and wherein the bulk properties of the solid are not modified when the composite material switches between the first form and second form, and which comprises:

(i) the neutral form of the switchable moiety bound to a surface via a linker X as in the structure of formula 3a, or 3b, or 3c, or any rotational isomers thereof,

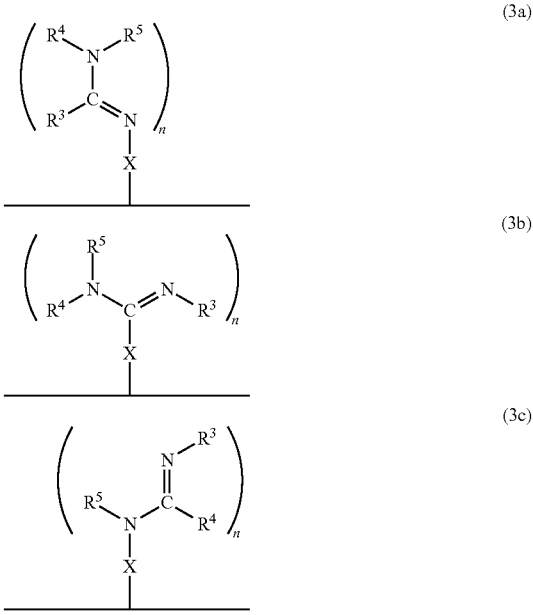

wherein:
N=CR³NR⁴R⁵, R³N=CNR⁴R⁵, R³NH=CR⁴NR⁵ are each switchable functional groups, wherein R³, R⁴, and R⁵ are independently H, a C₁ to C₁₀ aliphatic group that is linear, branched, or cyclic; a $C_kSi_m$ group where k and m are independently a number from 0 to 10 and k+m is a number from 1 to 10, a $C_5$ to $C_{10}$ aryl group, or a heteroaryl group having from 4 to 10 carbon atoms in the aromatic ring, each of which may be substituted; or, any combination of $R^3$, $R^4$, and $R^5$, together with the atoms to which they are attached, are connected to form a cycle, or heterocycle, each of which may be substituted;

n is an integer 1, 2 or 3; and

X is bonded to the solid and the switchable functional group and is a monovalent or a divalent moiety, or, X is a monovalent or a divalent cycle, or heterocycle, each of which may be substituted; optionally, X and one or two of $R^3$, $R^4$, and $R^5$, together with the atoms to which they are attached, are connected to form a cycle, or heterocycle, each of which may be substituted; and, wherein the alkylene, alkenylene and alkynylene moieties of X optionally comprise one or more amine, amide, ether, ester, thioether, thioester, silane, siloxane, or a combination thereof, within the hydrocarbon chain;

or (ii) the ionized form of the switchable moiety bound to a surface via a spacer X as in the structure of formula 4a, or 4b, or 4c, or any rotational isomers thereof,

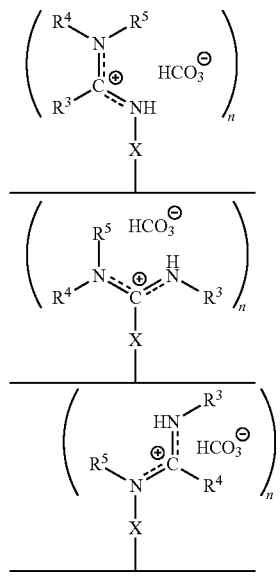

wherein:

$(N=CR^3NR^4R^5)^+$, $(R^3N=CNR^4R^5)^+$, $(R^3NH=CR^4NR^5)^+$ are each switchable functional groups, wherein $R^3$, $R^4$, and $R^5$ are independently H, a $C_1$ to $C_{10}$ aliphatic group that is linear, branched, or cyclic; a $C_kSi_m$ group where k and m are independently a number from 0 to 10 and k+m is a number from 1 to 10, a $C_5$ to $C_{10}$ aryl group, or a heteroaryl group having from 4 to 10 carbon atoms in the aromatic ring, each of which may be substituted; or, any combination of $R^3$, $R^4$ and $R^5$, together with the atoms to which they are attached, are connected to form a cycle, or heterocycle, each of which may be substituted;

n is an integer 1, 2 or 3; and

X is bonded to the solid and the switchable functional group and is a monovalent or a divalent moiety; or, X is a monovalent or a divalent cycle, or heterocycle, each of which may be substituted; optionally, X and one or two of $R^3$, $R^4$, and $R^5$, together with the atoms to which they are attached, are connected to form a cycle, or heterocycle, each of which may be substituted; and, wherein the alkylene, alkenylene and alkynylene moieties of X optionally comprise one or more amine, amide, ether, ester, thioether, thioester, silane, siloxane, or a combination thereof, within the hydrocarbon chain.

2. The composite material of claim 1, wherein n is 1 and/or $R^3$, $R^4$, and $R^5$ are methyl.

3. A composite material that is reversibly switchable between a first form and a second form, said composite material comprising a solid and solid-supported switchable moiety attached to said solid via a linker, wherein the attachment to said solid does not comprise a Si—O—Si or S—Au bond, the switchable moiety comprising a functional group that is switchable between a neutral form associated with said first form of said composite material, and an ionized form associated with said second form of the composite material, wherein the linker is not a polyamine, and wherein the bulk properties of the solid are not modified when the composite material switches between the first form and second form, wherein the solid is a polymeric material, a silica-based material that is glass, mesoporous silica or silica gel, each of which is optionally substituted or functionalized, or a semi-metallic material, or a metallic composite material.

4. The composite material of claim 3, wherein (i) said first form of the composite material is neutral and hydrophobic and the second form of the composite material is ionized and hydrophilic; and/or (ii) the composite material converts to or is maintained in said second form when the switchable moiety is exposed to $CO_2$ at an amount sufficient to maintain said switchable moiety in its ionized form, and wherein the composite material converts to or is maintained in said first form when $CO_2$ is removed or reduced to an amount insufficient to maintain said switchable moiety in its ionized form.

5. The composite material of claim 3, which comprises:

(i) the neutral form of the switchable moiety bound to a surface via a linker X as in the structure of formula 1,

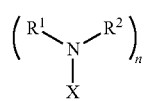

(1)

wherein:

$NR^1R^2$ is a switchable functional group, wherein $R^1$ and $R^2$ are each independently H, a $C_1$ to $C_{10}$ aliphatic group that is linear, branched, or cyclic, a $C_kSi_m$ group where k and m are independently a number from 0 to 10 and k+m is a number from 1 to 10, a $C_5$ to $C_{10}$ aryl group, or a heteroaryl group having 4 to 10 ring atoms, each of which may be substituted; or $R^1$ and $R^2$, together with the atoms to which they are attached, are connected to form a cycle, or heterocycle, each of which may be substituted;

n is an integer 1, 2 or 3; and

X is bonded to the solid and the switchable functional group and is a monovalent or a divalent moiety; or, X is a monovalent or a divalent cycle, or heterocycle, each of which may be substituted; optionally, X and $R^1$, X and $R^2$ or both, together with the atoms to which they are attached, are connected to form a cycle, or heterocycle, each of which may be substituted; and, wherein the alkylene, alkenylene and alkynylene moieties of X optionally comprise one or more amine, amide, ether, ester, thioether, thioester, silane, siloxane, or a combination thereof, within the hydrocarbon chain;
or
(ii) the ionized form of the switchable moiety bound to a surface via a linker X as in the structure of formula 2,

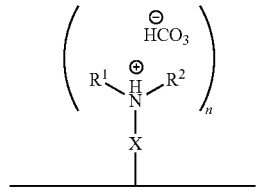

wherein:
$NR^1R^{2+}$ is a switchable functional group, wherein $R^1$ and $R^2$ are each independently H, a $C_1$ to $C_{10}$ aliphatic group that is linear, branched, or cyclic, a $C_kS_{im}$ group where k and m are independently a number from 0 to 10 and k+m is a number from 1 to 10, a $C_5$ to $C_{10}$ aryl group, or a heteroaryl group having 4 to 10 ring atoms, each of which may be substituted; or $R^1$ and $R^2$, together with the atoms to which they are attached, are connected to form a cycle, or heterocycle, each of which may be substituted;
n is an integer 1, 2 or 3; and
X is bonded to the solid and the switchable functional group and is a monovalent or a divalent moiety; or, X is a monovalent or a divalent cycle, or heterocycle, each of which may be substituted; optionally, X and $R^1$, X and $R^2$ or both, together with the atoms to which they are attached, are connected to form a cycle, or heterocycle, each of which may be substituted; and, wherein the alkylene, alkenylene and alkynylene moieties of X optionally comprise one or more amine, amide, ether, ester, thioether, thioester, silane, siloxane, or a combination thereof, within the hydrocarbon chain.

6. The composite material of claim 5, wherein n is 1 and/or $R^1$ and $R^2$ are ethyl.

7. The composite material of claim 3, wherein the polymeric material is a polymeric bead, a thin film, or a monolith; and/or an epoxide porous polymer, a methacrylate polymer, and/or methacrylate copolymer, each of which may be substituted or cross-linked.

8. The composite material of claim 3, wherein the semi-metallic or metallic composite material is steel, silicon wafers, silicon oxides, or goldfilms, each of which is optionally alloyed or functionalized.

9. The composite material of claim 3, wherein;
(i) the surface of the solid is rough; and/or
(ii) the surface of the solid is rough, and the rough surface imparts superhydrophobic properties on the first form of the composite material, and/or superhydrophilic properties on the second form of the composite material.

10. A method for removing water from non-aqueous solvents, or for removing water vapour from gaseous mixtures comprising utilizing a composite material as a drying agent, wherein the composite material is reversibly switchable between a first form and a second form, said composite material comprising a solid and solid-supported switchable moiety attached to said solid via a linker, wherein the attachment to said solid does not comprise a Si—O—Si or S—Au bond, the switchable moiety comprising a functional group that is switchable between a neutral form associated with said first form of said composite material, and an ionized form associated with said second form of the composite material, wherein the linker is not a polyamine, and wherein the bulk properties of the solid are not modified when the composite material switches between the first form and second form.

11. The method of claim 10, wherein once the composite material is rendered ionized and hydrophilic, it is separated from the mixture; or, once the composite material is rendered neutral and hydrophobic, it is separated from the mixture.

12. A method for separating or isolating an analyte from a sample comprising utilizing a composite material as a chromatographic support and/or stationary phase, wherein the composite material is reversibly switchable between a first form and a second form, said composite material comprising a solid and solid-supported switchable moiety attached to said solid via a linker, wherein the attachment to said solid does not comprise a Si—O—Si or S—Au bond, the switchable moiety comprising a functional group that is switchable between a neutral form associated with said first form of said composite material, and an ionized form associated with said second form of the composite material, wherein the linker is not a polyamine, and wherein the bulk properties of the solid are not modified when the composite material switches between the first form and second form, and, wherein the support and/or stationary phase is used in gas chromatography and/or solid phase extraction columns or cartridges.

13. The method of claim 12, wherein the composite material is used as a chromatographic stationary support for liquid chromatography (LC), high performance liquid chromatography (HPLC) or ultra-performance liquid chromatography (UPLC); or, used as a chromatographic stationary support for supercritical fluid chromatography (SFC).

14. The method of claim 13, wherein when the composite material is used as a chromatographic stationary support for LC, HPLC, or UPLC, the chromatographic stationary support is eluted using an eluting solvent with varying $CO_2$ content such that the hydrophilicity of the composite material varies over time during elution.

15. The method of claim 13, wherein when the composite material is used as a chromatographic stationary support for SFC, the chromatographic stationary support is eluted using an eluting solvent with varying water content such that the hydrophilicity of the composite material varies over time during elution.

* * * * *